United States Patent [19]
Bosslet et al.

[11] Patent Number: 5,591,828
[45] Date of Patent: Jan. 7, 1997

[54] BISPECIFIC AND OLIGOSPECIFIC MONO-AND OLIGOVALENT RECEPTORS, THE PREPARATION AND USE THEREOF

[75] Inventors: Klaus Bosslet; Peter Hermentin; Gerhard Seemann, all of Marburg; Ludwig Kuhlmann, Flörsheim am Main; Axel Steinsträsser, Liederbach, all of Germany

[73] Assignee: Behringwerke Aktiengesellschaft, Marburg, Germany

[21] Appl. No.: 317,612

[22] Filed: Sep. 29, 1994

Related U.S. Application Data

[63] Continuation of Ser. No. 147,428, Nov. 5, 1993, abandoned, which is a continuation of Ser. No. 17,439, Feb. 12, 1993, abandoned, which is a continuation of Ser. No. 541,020, Jun. 20, 1990, abandoned.

[30] Foreign Application Priority Data

Jun. 22, 1989 [DE] Germany .................. 39 20 358.1

[51] Int. Cl.$^6$ .................. C07K 16/46; C07K 16/28
[52] U.S. Cl. .................. 530/387.3; 435/188.5; 530/389.7; 530/388.8
[58] Field of Search .............. 435/69.6; 530/387.3, 530/395, 388.8; 424/133.1, 155.1

[56] References Cited

U.S. PATENT DOCUMENTS

| | | | |
|---|---|---|---|
| 4,652,440 | 3/1987 | Paik et al. | 424/1.1 |
| 4,714,681 | 12/1987 | Reading | 435/240.27 |

FOREIGN PATENT DOCUMENTS

| | | |
|---|---|---|
| 0141079A3 | 5/1985 | European Pat. Off. . |
| 0369566A2 | 5/1990 | European Pat. Off. . |
| 369566 | 5/1990 | European Pat. Off. . |
| WO86/01407 | 3/1986 | WIPO . |

OTHER PUBLICATIONS

H. Paulus, Behring Inst. Mitt. 78, (1985) 118–132.
U. D. Staerz and M. J. Bevan, Proc. Natl. Acad. Sci. USA 83, (1986) 1453–1457.
U. Zimmerman, Rev. Physio. Biochem. Pharmacol 105 (1986), 176–260.
J. Van Duk et al., Int. J. Cancer 43, (1989) 344–349.
M. W. Brechbiel et al., Inorganic Chemistry 25, (1986) 2772–2781.
Shulman et al., Nature 276, (1978) 269.
Cordell et al., J. Histochem. Cytochem. 32, (1984) 219.
Molecular Cloning, A Laboratory Manual; Sambrook, Fritsch, Maniatis; Cold Spring Harbor Laboratory, 1982, (S. 11–44, 51–127, 133–134, 141, 146, 150–167, 170, 188–193, 197–199, 248–255, 270–294, 310–328, 364–401, 437–506).
Molecular Cloning, A Laboratory Manual; Sambrook, Fritsch, Maniatis; Cold Spring Harbor Laboratory Press, 1989, (S. 16.2–16.22, 16.30–16.40, 16.54–16.55).
A. M. Frischauf et al., J. Mol. Biol. 170, (1983) 827–842.
G. H. A. Seeman et al., The EMBO Journal 5, (1986) 547–552.
Orlandi et al., Proc. Natl. Acad. Sci., USA 86, (1989) 3833–3837.
Simon et al., Nucl. Acids Res. 16, (1988) 354.
P. L. Ey et al., Immunochemistry 15, (1978) 429.
E. K. O'Shea et al., Science 245, (1989) 646–648.
J. P. Tam et al., J. Am. Chem. Soc. 105, (1983) 6442–6455.
J. Rivier et al., J. Chromatography 288, (1984) 303–328.
Beidler et al., The Journal of Immunology 141(11): 4053–60 (1988).
Williams, Trends in Biotechnology 6(2): 36–39, 42 (1988).
V. T. Oi & S. L. Morrison, Biotechnique 4(3): 214–21 (1986).
Tao et al. Journal of Immunology vol. 143 p. 2595 1989.
Osbund et al. Immunology Today, vol. 11, No. 6 p. 193 1990.
Waldmann, Science vol. 252 p. 1657 1991.
Harris et al. TibTech vol. 11 p. 42 1993.
Stanfield et al. TibTech vol. 12 1994 p. 275.
Hird et al. Genes and Cancer p. 183, 1990 ed. Carney and Sikora.
Lazar et al. Molecular and Cellular Biology p. 1247, 1988.
Gillies et al. Human Antibodies & Hybridomers 1(1) 1990 p.47.
Burgess et al. Journal of Cell Biology vol. 111 1990 p. 2129.
Huston et al. PNAS. vol. 85 5879, 1988.
Titus et al Journal of Immunology vol. 139 3153 N1 1987.

*Primary Examiner*—Lila Feisee
*Attorney, Agent, or Firm*—Finnegan, Henderson, Farabow, Garrett & Dunner, L.L.P.

[57] ABSTRACT

The invention relates to bispecific and oligospecific, mono- and oligovalent receptors which are prepared by gene manipulation by fusion of DNA coding for F(ab) fragments of antibodies of two or more different specificities by means of suitable linkers. In this connection, one specificity is preferably directed either against an epitope, which is located on the cell membrane or in the interstitium, of a tumor-associated antigen (TAA) or against an epitope in the tumor endothelium (TE), while the other specificities relate to high-molecular or low-molecular weight ligands and react, for example, with the Komplexons ethylenediaminetetraacetate and diethylenetriaminepentaacetate in Y90 complexed form (EDTA-Y90 and DTPA-Y90 respectively). In a particularly preferred embodiment, the binding with the Komplexons takes place on the Komplexon receptor arm via fos-jun interaction (or else avidin-biotin interaction). Other preferred specificities have catalytic properties.

10 Claims, 22 Drawing Sheets

POLYPEPTIDE SPACER

POLYPEPTIDE SPACER

VH

```
    Q   V   Q   L   Q   E   S   G   G   G   L   V   Q   P   G   G   S   L   R   L
CAGGTCCAACTGCAGGAGTCTGGAGGAGGCTTGGTACAGCCTGGGGGTTCTCTGAGACTC
         10        20        30        40        50        60

S   C   A   T   S   G   F   S   D   Y   Y   M   N   W   V   R   Q   P   P   G
TCCTGCGCAACTTCTGGGTTCAGTGATTACTACATGAACTGGGTCCGCCAGCCTCCAGGA
         70        80        90       100       110       120

K   A   L   E   W   L   G   F   I   S   N   K   P   N   G   H   T   T   E   Y
AAAGCACTTGAGTGGTTGGGTTTTATTTCAAACAAACCTAATGGTCACACAACAGAGTAC
        130       140       150       160       170       180

S   A   S   V   K   G   R   F   T   I   S   R   D   N   S   Q   S   I   L   Y
AGTGCATCTGTGAAGGGTCGGTTCACCATCTCCAGAGATAATTCCCAAAGCATCCTCTAT
        190       200       210       220       230       240

L   Q   M   N   T   L   R   A   E   D   S   A   T   Y   Y   C   A   R   D   K
CTTCAAATGAACACCCTGAGAGCTGAGGACAGTGCCACTTATTATTGTGCAAGAGATAAG
        250       260       270       280       290       300

G   I   R   W   Y   F   D   V   W   G   Q   G   T   T   V   T   V   S   S
GGAATACGATGGTACTTCGATGTCTGGGGCCAAGGGACCACGGTCACCGTCTCCTCA
        310       320       330       340       350
```

VK

```
    A   I   L   S   A   S   P   G   E   K   V   T   M   T   C   R   A   S   S   S
AGCAATCCTGTCTGCATCTCCAGGGGAGAAGGTCACAATGACTTGCAGGGCCAGCTCAAG
         10        20        30        40        50        60

V   S   Y   M   H   W   Y   Q   Q   K   P   G   S   S   P   K   P   W   I   Y
TGTAAGTTACATGCACTGGTACCAGCAGAAGCCAGGATCCTCCCCCAAACCCTGGATTTA
         70        80        90       100       110       120

A   T   S   N   L   A   S   G   V   P   A   R   F   S   G   S   G   S   G   T
TGCCACATCCAACCTGGCTTCTGGAGTCCCTGCTCGCTTCAGTGGCAGTGGGTCTGGGAC
        130       140       150       160       170       180

S   Y   S   L   T   I   I   R   V   E   A   E   D   A   A   T   Y   Y   C   Q
CTCTTACTCTCTCACAATCATCAGAGTGGAGGCTGAAGATGCTGCCACTTATTACTGCCA
        190       200       210       220       230       240

Q   W   S   S   N   P   L   T   F   G   A   G   T   K   L   E   I
GCAGTGGAGTAGTAACCCGCTCACGTTCGGTGCTGGGACCAAGCTGGAGATC
        250       260       270       280       290
```

```
 L  Q  E  S  G  P  D  L  V  K  P  S  Q  S  L  S  L  T  C  T
CTGCAGGAGTCAGGACCTGACCTGGTGAAACCTTCTCAGTCACTTTCACTCACCTGCACT
         10        20        30        40        50        60

V  T  G  Y  S  I  T  S  G  Y  S  W  H  W  I  R  Q  F  P  G
GTCACTGGCTACTCCATCACCAGTGGTTATAGCTGGCACTGGATCCGGCAGTTTCCAGGA
         70        80        90       100       110       120

N  K  L  E  W  M  G  Y  I  Q  Y  S  G  I  T  N  Y  N  P  S
AACAAACTGGAATGGATGGGCTACATACAGTACAGTGGTATCACTAACTACAACCCCTCT
        130       140       150       160       170       180

L  K  S  R  I  S  I  T  R  D  T  S  K  N  Q  F  F  L  Q  L
CTCAAAAGTCGAATCTCTATCACTCGAGACACATCCAAGAACCAGTTCTTCCTGCAGTTG
190       200       210       220       230       240

N  S  V  T  T  E  D  T  A  T  Y  Y  C  A  R  E  D  Y  D  Y
AATTCAGTGACTACTGAGGACACAGCCACATATTACTGTGCAAGAGAAGACTATGATTAC
         250       260       270       280       290       300

H  W  Y  F  D  V  W  G  A  G  T  T  V  T  V  S  S
CACTGGTACTTCGATGTCTGGGGCGCAGGGACCACGGTCACCGTCTCCTCA
         310       320       330       340       350
```

VK

```
 L  T  Q  S  P  A  I  M  S  A  S  L  G  E  E  I  T  L  T  C
CTGACCCAGTCTCCAGCAATCATGTCTGCATCTCTAGGGGAGGAGATCACCCTAACCTGC
         10        20        30        40        50        60

S  T  S  S  S  V  S  Y  M  H  W  Y  Q  Q  K  S  G  T  S  P
AGTACCAGCTCGAGTGTAAGTTACATGCACTGGTACCAGCAGAAGTCAGGCACTTCTCCC
         70        80        90       100       110       120

K  L  L  I  Y  S  T  S  N  L  A  S  G  V  P  S  R  F  S  G
AAACTCTTGATTTATAGCACATCCAACCTGGCTTCTGGAGTCCCTTCTCGCTTCAGTGGC
        130       140       150       160       170       180

S  G  S  G  T  F  Y  S  L  T  I  S  S  V  E  A  E  D  A  A
AGTGGGTCTGGGACCTTTTATTCTCTCACAATCAGCAGTGTGGAGGCTGAAGATGCTGCC
         190       200       210       220       230       240

D  Y  Y  C  H  Q  W  S  S  Y  P  T  F  G  G  G  T  K  L  E
GATTATTACTGCCATCAGTGGAGTAGTTATCCCACGTTCGGAGGGGGGACCAAGCTGGAG
         250       260       270       280       290       300
```

```
  Q   V   Q   L   Q   Q   S   G   P   E   L   V   K   P   G   A   S   V   K   M
CAGGTCCAACTGCAGCAGTCTGGACCTGAGCTGGTAAAGCCTGGGGCTTCAGTGAAGATG
         10        20        30        40        50        60

S   C   K   A   S   G   Y   T   F   T   Y   Y   V   I   H   W   V   K   Q   K
TCCTGCAAGGCTTCTGGATACACATTCACTTACTATGTTATTCACTGGGTGAAACAGAAG
         70        80        90       100       110       120

P   G   Q   G   L   E   W   I   G   Y   I   H   P   Y   N   A   G   T   E   Y
CCTGGGCAGGGCCTTGAGTGGATTGGATACATTCATCCTTACAATGCTGGTACTGAGTAC
        130       140       150       160       170       180

N   E   K   F   K   G   K   A   T   L   T   S   D   K   S   S   S   T   A   Y
AATGAGAAGTTCAAAGGCAAGGCCACACTGACTTCAGACAAATCCTCCAGCACAGCCTAC
        190       200       210       220       230       240

M   E   L   S   S   L   T   S   E   D   S   A   V   Y   Y   C   S   M   G   R
ATGGAGCTCAGCAGCCTGACCTCTGAGGACTCTGCGGTCTATTACTGTTCAATGGGACGA
        250       260       270       280       290       300

G   G   D   Y   W   G   Q   G   T   T   V   T   V   S   S
GGGGGTGACTACTGGGGCCAAGGGACCACGGTCACCGTCTCCTCA
        310       320       330       340
```

VK

```
  L   T   Q   S   P   A   I   M   S   A   S   P   G   E   K   V   T   M   T   C
CTGACCCAGTCTCCAGCAATTATGTCTGCATCTCCTGGGGAGAAGGTCACCATGACCTGC
         10        20        30        40        50        60

S   A   S   S   S   V   S   Y   M   H   W   Y   Q   Q   K   S   G   T   S   P
AGTGCCAGCTCAAGTGTAAGTTACATGCACTGGTACCAGCAGAAGTCAGGCACCTCCCCC
         70        80        90       100       110       120

K   R   W   I   Y   D   T   S   K   L   A   S   G   V   P   A   R   F   S   G
AAAAGATGGATTTATGACACATCCAAACTGGCTTCTGGAGTCCCTGCTCGCTTCAGTGGC
        130       140       150       160       170       180

S   G   S   G   T   S   Y   S   L   T   I   S   S   M   E   A   E   D   A   A
AGTGGGTCTGGGACCTCTTACTCTCTCACAATCAGCAGCATGGAGGCTGAAGATGCTGCC
        190       200       210       220       230       240

T   Y   Y   C   Q   Q   W   S   S   N   P   F   T   F   G   A   G   T   K   L
ACTTATTACTGCCAGCAGTGGAGTAGTAACCCATTCACGTTCGGCGCGGGGACCAAGCTG
        250       260       270       280       290       300
```

```
  A   E   S   G   P   G   L   V   R   L   T   S   L   S   I   T   C   T   V   S
GCAGAGTCAGGGCCTGGCCTGGTGCGCCTCACGAGCCTGTCCATCACTTGCACTGTCTCT
         10        20        30        40        50        60

G   F   S   L   I   S   Y   G   V   H   W   V   R   Q   P   P   G   K   G   L
GGCTTTTCATTAATTAGTTATGGTGTACACTGGGTTCGCCAGCCTCCAGGAAAGGGTCTG
         70        80        90       100       110       120

E   W   L   G   V   I   W   A   G   G   S   T   N   Y   N   S   A   L   M   S
GAGTGGCTGGGAGTAATATGGGCAGGTGGAAGCACAAATTATAATTCGGCTCTCATGTCC
        130       140       150       160       170       180

R   L   S   I   S   K   D   N   S   K   S   Q   V   F   L   K   M   N   S   L
AGACTGAGCATCAGCAAAGACAACTCCAAGAGCCAAGTTTTCTTAAAAATGAACAGTCTG
        190       200       210       220       230       240

Q   T   G   D   T   A   I   Y   Y   C   A   R   G   G   D   D   Y   D   G   F
CAAACTGGTGACACAGCCATATACTACTGTGCCAGAGGGGGGGATGATTACGATGGGTTT
        250       260       270       280       290       300

A   Y   W   G   Q   G   T   T   V   T   V   S   S   G   E   S
GCTTACTGGGGCCAAGGGACCACGGTCACCGTCTCCTCAGGTGAGTCC
        310       320       330       340
```

VK

```
  L   T   Q   S   P   S   S   L   A   V   S   A   G   E   K   V   T   M   S   C
CTGACCCAGTCTCCATCCTCCCTGGCTGTGTCAGCAGGAGAGAAGGTCACTATGAGCTGC
         10        20        30        40        50        60

K   S   S   Q   S   L   L   S   S   T   K   R   K   N   Y   L   A   W   Y   Q
AAATCCAGTCAGAGTCTGCTCAGCAGTACAAAGCGAAAGAACTACTTGGCTTGGTACCAG
         70        80        90       100       110       120

Q   K   P   G   Q   S   P   K   L   L   I   Y   W   A   S   T   R   E   S   G
CAGAAACCAGGTCAGTCTCCTAAACTACTGATCTACTGGGCATCCACTCGGGAATCTGGG
        130       140       150       160       170       180

Y   P   D   R   F   T   G   S   G   S   G   T   D   F   T   L   T   I   S   S
GTCCCTGATCGCTTCACAGGCAGTGGATCTGGGACAGATTTCACTCTCACCATCAGCAGT
        190       200       210       220       230       240

V   Q   A   E   D   L   A   V   Y   Y   C   K   Q   S   Y   N   L   R   A   F
GTGCAGGCTGAAGACCTGGCAGTTTATTACTGCAAACAATCTTATAATCTTCGGGCGTTC
        230       260       270       280       290       300

G   G   G   T   K   L   E   I   K
GGTGGAGGGACCAAGCTGGAGATCAAA
        310       320
```

FIG. 25

BISPECIFIC AND OLIGOSPECIFIC MONO-AND OLIGOVALENT RECEPTORS, THE PREPARATION AND USE THEREOF

This application is a continuation, of application Ser. No. 08/147,428, filed Nov. 5, 1993, now abandoned, which is a continuation of application Ser. No. 8/017,439 filed Feb. 12, 1993, abandoned; which is a continuation of application Ser. No. 07/541,020 filed Jun. 20, 1990, now abandoned.

The invention relates to bispecific and oligospecific, mono- and oligovalent receptors which are prepared by gene manipulation by fusion of DNA coding for F(ab) fragments of antibodies of two or more different specificities by means of suitable linkers. In this connection, one specificity is preferably directed either against an epitope of a tumor-associated antigen (TAA), which is located on the cell membrane or in the interstitium or against an epitope in the tumor endothelium (TE), while the other specificities relate to high-molecular or low-molecular weight ligands and react, for example, with the chelates ethylenediaminetetraacetate and diethylenetriaminepentaacetate in Y90 complexed form (EDTA-Y90 and DTPA-Y90 respectively). In a particularly preferred embodiment, the binding with the chelates takes place on the chelate receptor arm via fos-jun interaction (or else avidin-biotin interaction). Other preferred specificities have catalytic properties, or bind to other TAA's on the same tumour cell or to receptors on lymphoid cells.

Bispecific antibodies have to date been prepared by the following methods chemical coupling of antibodies of diverse specificity via heterobifunctional linkers (H. Paulus, Behring Inst. Mitt. 78, (1985), 118–132)

fusion of hybrids which are already available and secrete various monoclonal antibodies (NAb), and isolation of the bispecific monovalent portion (U. S. Staerz and M. J. Bevan, Proc. Natl. Acad. Sci. U.S.A. 83, (1986) 1453–1457)

transfection of the light and heavy chain genes of two different Mabs (4 genes) into murine myeloma cells or other eukaryotic expression systems and isolation of the bispecific monovalent portion (U. Zimmermann, Rev. Physio. Biochem. Pharmacol. 105 (1986), 176–260; J. van Dijk et al., Int. J. Cancer 43, (1989), 344–349).

Bispecific antibodies of this type are employed for the therapy and diagnosis of malignant tumors. The principle of the process comprises, in the first step, achieving saturation of the epitopes which are recognized by one of the two specificities on the target cells, by injection of the bispecific macromolecule over prolonged periods and with high doses.

In the second step, which comprises interruption of the treatment for several days, there is autoelimination of the non-specifically adsorbed bispecific antibody from the non-target tissues.

This autoelimination can be speeded up by injection of an anti-idiotype antibody which is coupled to sugar residues, preferably galactose, and is directed against the anti-tumor arm of the bispecific receptor.

The third step in the process comprises i.v. injection of a radiolabeled, hydrophilic low-molecular weight ligand which does not accumulate in cells, has a short residence time in the body, has high complexing constants for beta- and gamma-emitters such as $^{90}Y$, $^{186}Re$, $^{188}Re$, $^{189}Re$, $^{99m}Tc$ or $^{111}$, and binds to the second specificity of the bispecific receptor with high affinity. This step results in a concentration of the radioactive ligand, associated with prolonged retention on the target tissue, which results in selective destruction of the target tissue and makes possible diagnosis of metastases, for example.

BRIEF DESCRIPTION OF THE DRAWINGS

FIG. 1 depicts the gene fragments which code for the $V_H$ and $C_H1$ sections of monoclonal antibodies a and b being linked in such a manner that the N-terminus of the $V_H$ domain of Mab b is covalently bonded via a polypeptide spacer to the C terminus of the $C_H1$ domain of MAb a.

FIG. 22 depicts the DNA and amino acid sequence of $V_H$ and $V_K$ for MAb A.

FIG. 23 depicts the DNA and amino acid sequence of $V_H$ and $V_K$ for MAb B.

FIG. 24 depicts the DNA and amino acid sequence of $V_H$ and $V_K$ for MAb C.

FIG. 25 depicts the DNA and amino acid sequence of $V_H$ and $V_K$ for MAb D.

Figure 1:
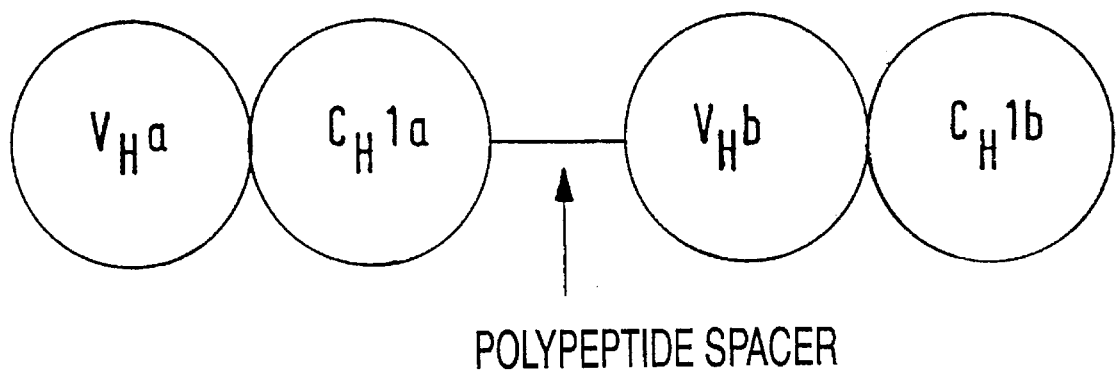
Figure 2:
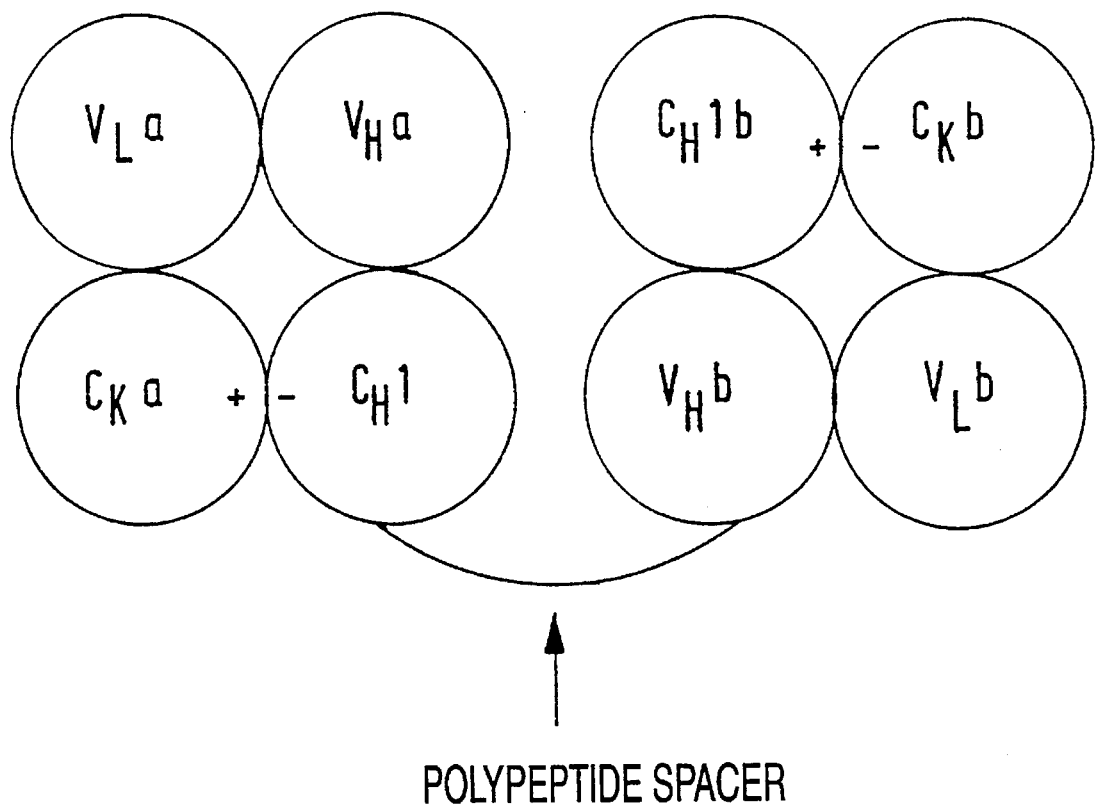
FIG. 2 depicts the preferential expression product when the gene construct of FIG. 1 is transfected together with the genes for the light chains of MAb a and MAb b into eukaryotic cells. The correct pairing of heavy and light chains is aided by modification of the $C_H1a$, $C_H1b$, $C_ka$ and $C_kb$ domains such that opposite charges meet at the constant domains or areas of contact which are each hydrophobic or each hydrophilic.

The invention now provides bispecific and oligospecific receptors which have, depending on requirements, mono- or oligovalent binding sites to the particular epitopes and are produced by gene manipulation by means of suitable linkers. This entails the gene fragments which code for the $V_H$ and $C_H1$ sections of antibodies a and b being linked, by means of suitable synthetic oligonucleotides as depicted by way of example in Tab. 1, in such a manner that the N-terminus of the $V_H$ domain of MAb b is covalently bonded via a polypeptide spacer to the C terminus of the $C_H1$ domain of MAb a (FIG. 1). The $V_HaC_Ha$-polypeptide spacer -$V_HbC_H1b$ gene construct is transfected together with the genes for the light chains of antibodies a and b into eukaryotic cells (for example mouse myeloma cells). The $C_H1a$, $C_H1b$, $C_ka$ and $C_kb$ domains are modified in such a way that opposite charges meet at the areas of contact of the constant domains ($C_H1a(+)C_ka(-)$; $C_H1b(-)C_kb(+)$) (+=positive, −=negative) or opposing areas of contact are in each case hydrophobic or in each case hydrophilic. This means that the transfectomas preferentially express hybrid molecules which have the correct pairings of heavy and light chains (FIG. 2).

Here, antibody a is a representative example of an anti-tumor antibody, and antibody b represents an antibody against a low-molecular weight ligand, preferably the chelates DTPA-Y90 or EDTA-Y90.

Bi- or oligospecific receptor accordingly means a genetically engineered construction of $V_H$ and $C_H1$ domains of antibodies of diverse specificity via suitable linkers so that the required mobility for association with the corresponding light chains is present and antigen binding is not impeded.

The antigen-binding sites are called valencies or binding sites. A bispecific monovalent receptor thus has one antigen-binding site in each case when there are two specificities. Consequently, a bispecific trivalent receptor has one antigen-binding site for one specificity and two antigen-binding sites for the other.

Figure 3:
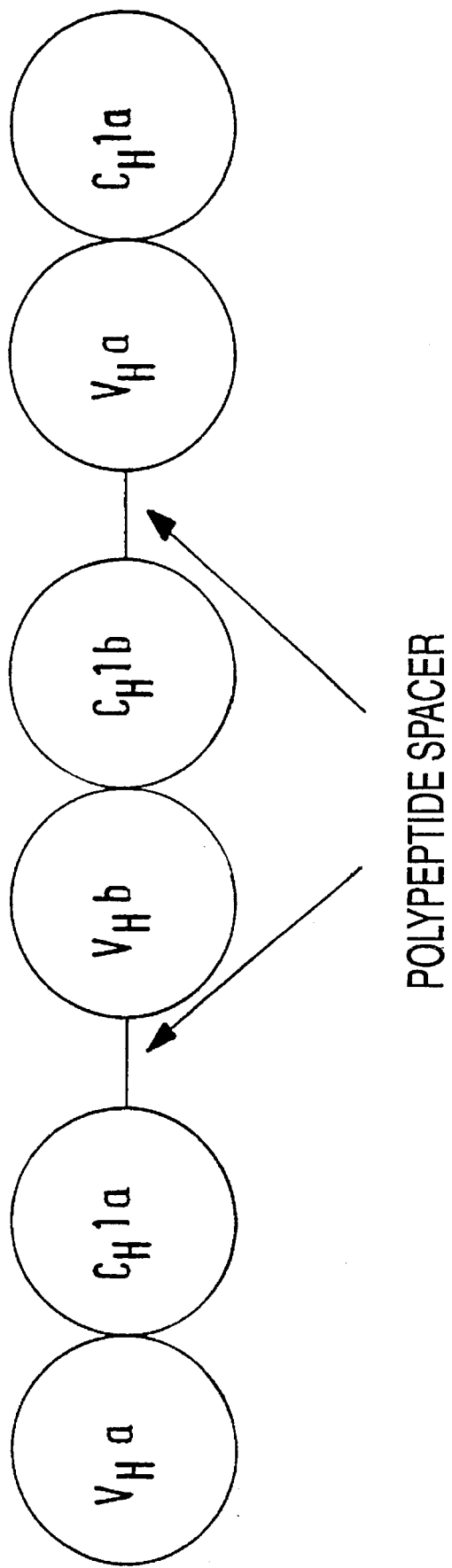
FIG. 3 depicts bispecific receptors that are bivalent for MAb a and monovalent for MAb b. The C-terminal end of the $C_H1$ domain of MAb b of the gene construct depicted in FIG. 1 is linked to the N-terminal end of the $V_H$ domain of MAb a by a polypeptide spacer.
Figure 4:
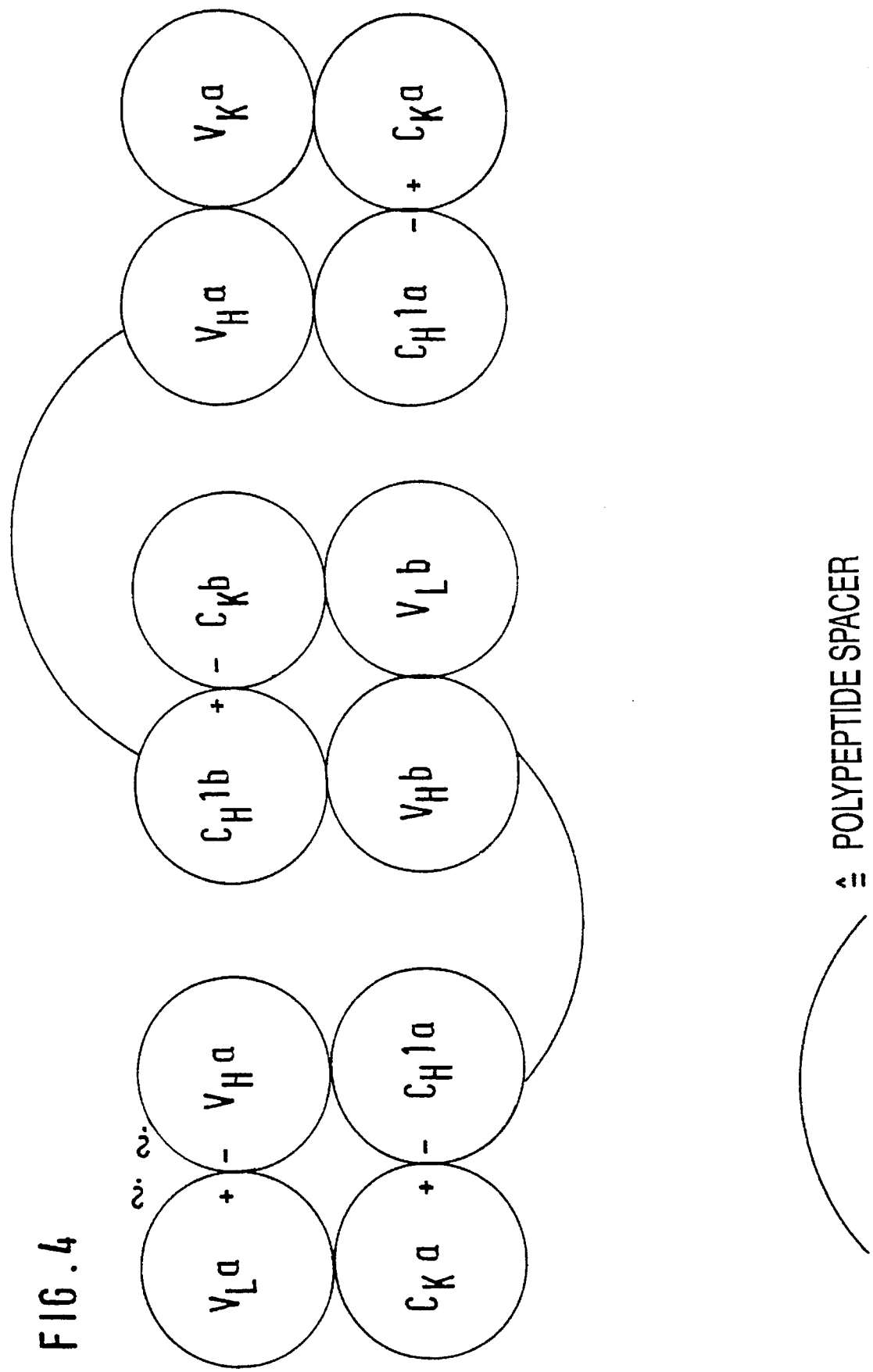
FIG. 4 depicts the preferential expression product when the gene construct depicted in FIG. 3 is transfected together with the genes for the light chains of MAb a and MAb b into eukaryotic cells. The fusion molecules expressed preferentially comprise two F(ab) fragments of MAb a and one F(ab) fragment of MAb b.

Bispecific receptors which are bivalent for the tumor antigen (MAb a) and monovalent for EDTA-Y90 (MAb b) are prepared by linking the heavy chain gene construct described above, by means of the abovementioned oligonucleotide linker, to the gene section which codes for the $V_H$ and $C_H1$ domains of MAb a (FIG. 3) so that the C-terminal end of the $C_H1$ domain of MAb b is connected to the N-terminal end of the $V_H$ domain of MAb a by a polypeptide spacer. These gene constructs are transfected together with the genes for the light chains belonging to MAb a and b into eukaryotic cells (for example myeloma cells). The $C_H1$ and $C_k$ domains are provided, as described above, with complementary charges or areas of contact which are in each case hydrophobic or hydrophilic. The transfectomas preferentially express fusion molecules which comprise two F(ab) fragments of MAb a and one F(ab) fragment of MAb b (FIG. 4). The mobility of the peptide linkers makes possible the alignment of the two F(ab) arms of MAb a towards the tumor cell with, at the same time, alignment of the F(ab) arm of MAb b towards the intercellular space. It is possible correspondingly to add further binding sites of identical or different specificity. Moreover, it is possible to combine freely the sequence of specificities in the constructs.

Consequently, the invention relates to bispecific or oligospecific, mono- or oligovalent receptors which have both specificity for an epitope located on the cell membrane or in the interstitium, for example TAA or TE, and specificity for a low- or high-molecular weight ligand which is distributed exclusively in the extracellular space. In this connection, one specificity is preferably formed by the tumor-specific antibodies, as proposed in German Patent Application P 39 09 799.4, whereas the other specificity is preferably directed against DTPA-Y90 or EDTA-Y90. In a particularly preferred embodiment, the binding takes place with chelates on the chelate receptor arm via fos-Jun interaction (see Example 5). Another preferred variant of the invention comprises the incorporation of specificities with catalytic activity. Moreover, there is no restriction on the choice of the sequence of the specificities or binding valencies, as is shown by way of example in FIG. 4 for three valencies with two specificities.

Particularly preferred constructs according to the invention are those which contain a V gene of Tables 2, 3, 4 and/or 5. Antibodies with these sequences and their properties are described in German Patent Application P 39 09 799.4. Moreover, the complementarity determining regions (CDRs) can be identified by the method of Kabat and Wu (Sequences of Proteins of Immunological Interest, U.S. Dept. of Health and Human Services, U.S. Government Printing Office (1987)). Likewise preferred are constructs which contain specificities against the epitopes defined by the monoclonal antibodies described above.

The invention additionally relates to genetic engineering processes for the preparation of the constructs described above, and to a use of the abovementioned constructs for preparing pharmaceuticals for controlling and diagnosing target cells. This entails, in a first step, saturation of the relevant epitopes on target cells after injection of the constructs and, in a subsequent interval, elimination of non-specifically adsorbed or unbound constructs. The step following this comprises injection and subsequent specific binding of a low- or high-molecular weight ligand which does not accumulate in cells and is intrinsically cytotoxic or is "activated" to cytotoxicity by extracorporeal influences where appropriate in another step. Examples of processes of this type are enzymatic activation, activation by microwave irradiation of a prodrug or activation by laser light.

The invention is furthermore contained in the examples and the patent claims.

EXAMPLE 1

Preparation of an anti-DTPA-Y90 or EDTA-Y90 MAb

Isothiocyanatobenzyl-DTPA (formula 2) was covalently coupled as hapten onto human serum albumin (HSA as carrier) with a degree of derivatization of 19 benzyl-DTPA molecules per HSA molecule by the method described in (N. W. Brechbiel et al., Inorganic Chemistry 25, (1986) 2772–2781). 20 µg of this hapten-carrier complex, into which cold Y had been complexed, were injected s.c. on day 0 with Freund's adjuvant, on day 7 and 14 with incomplete Freund's adjuvant and on day 21 with PBS into Balb/c mice. On day 24, the spleens of the mice with the highest anti-DTPA antibody titers were fused with the SP2/0-Ag14 myeloma cell line (Shulman et al., Nature 276, (1978) 269). The resulting hybridomas were tested in a DTPA-specific ELISA for the production of high-affinity MAbs against DTPA and EDTA. The ELISA comprised a solid phase which was loaded with a solution containing HSA-benzyl-DTPA-Y. The supernatant containing the MAb to be tested was preincubated with free chelate or its metal ion complexes, and its binding to the specific solid phase was measured. An enzyme amplification system which is coupled to an anti-mouse immunoglobulin antibody was used for this purpose. The details of these methods are described in Annex 1a and 1b.

MAbs which have the properties described in Annex 1e were obtained using this assay system.

In contrast to many other anti-DTPA/EDTA MAbs, these MAbs do not bind to normal human tissue, as was found using the APAAP technique (Cordell et al., J. Histochem. Cytochem. 32: 219, 1984) on cryopreserved tissues. It is therefore possible to use these MAbs in vivo for diagnosis and therapy.

The competitors employed were the chelates DTPA and EDTA in non-complexed and in complexed form (Annex 1c).

In addition, the structurally related compounds transaconitic acid and 1,2-diaminoethane were used as inhibitors (see Annex 1e). MAb BW 2050/174 is particularly suitable for in vivo use, showing preferential binding to EDTA-Y, in contrast to all the other MAbs (see Annex 1e, low competitor excess for EDTA-Y (100×) higher excess for other EDTA Komplexons). The hybrid 2050/174 was therefore stabilized and used for developing the EDTA-Y arm in the bispecific receptor.

EXAMPLE 2

Preparation and expression of a $V_H$1a $C_H$1-linker-$V_H$1b $C_H$1 gene construct The techniques used here were taken, unless indicated otherwise, from Molecular Cloning, A Laboratory Manual; Sambrook, Fritsch, Maniatis; Cold Spring Harbor Laboratory, 1982 (pp. 11–44, 51–127, 133–134, 141, 146, 150–167, 170, 188–193, 197–199, 248–255, 270–294, 310–328, 364–401, 437–506) and from Molecular Cloning, A Laboratory Manual, Second Edition; Sambrook, Fritsch, Maniatis; Cold Spring Harbor Laboratory Press, 1989, (pp. 16.2–16.22, 16.30–16.40, 16.54–16.55).

A human $IgG_3$ C gene was isolated from a human gene bank in EMBL3 phages (A. M. Frischauf et al., J. Mol. Biol. 170, 827–842 (1983) and G. H. A. Seemann et al., The EMBO Journal 5 (1986), 547–552).

Figure 5:
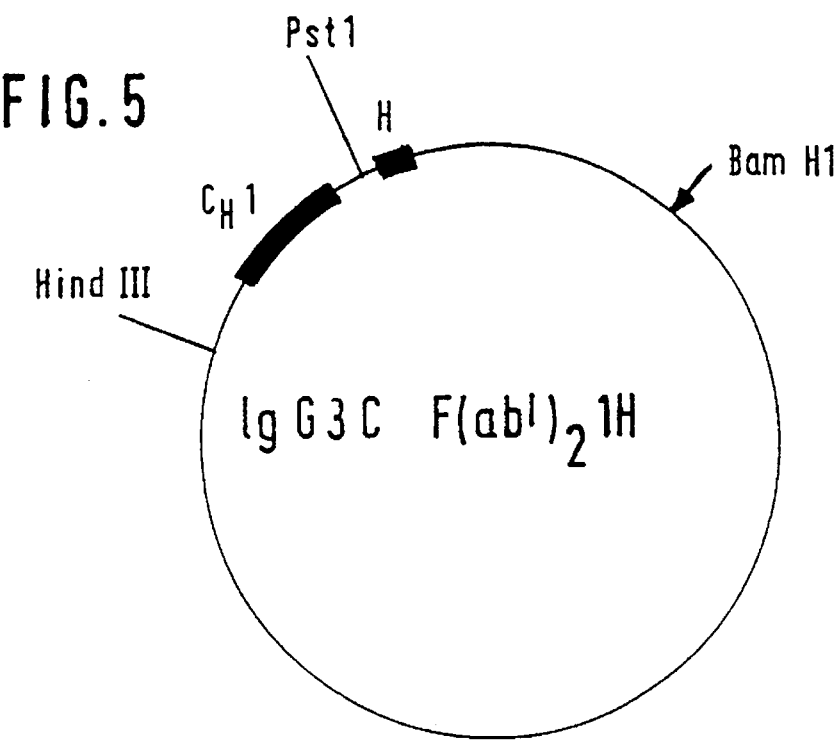
FIG. 5 depicts a plasmid containing the $C_H1$ exon and a hinge exon.
Figure 6:
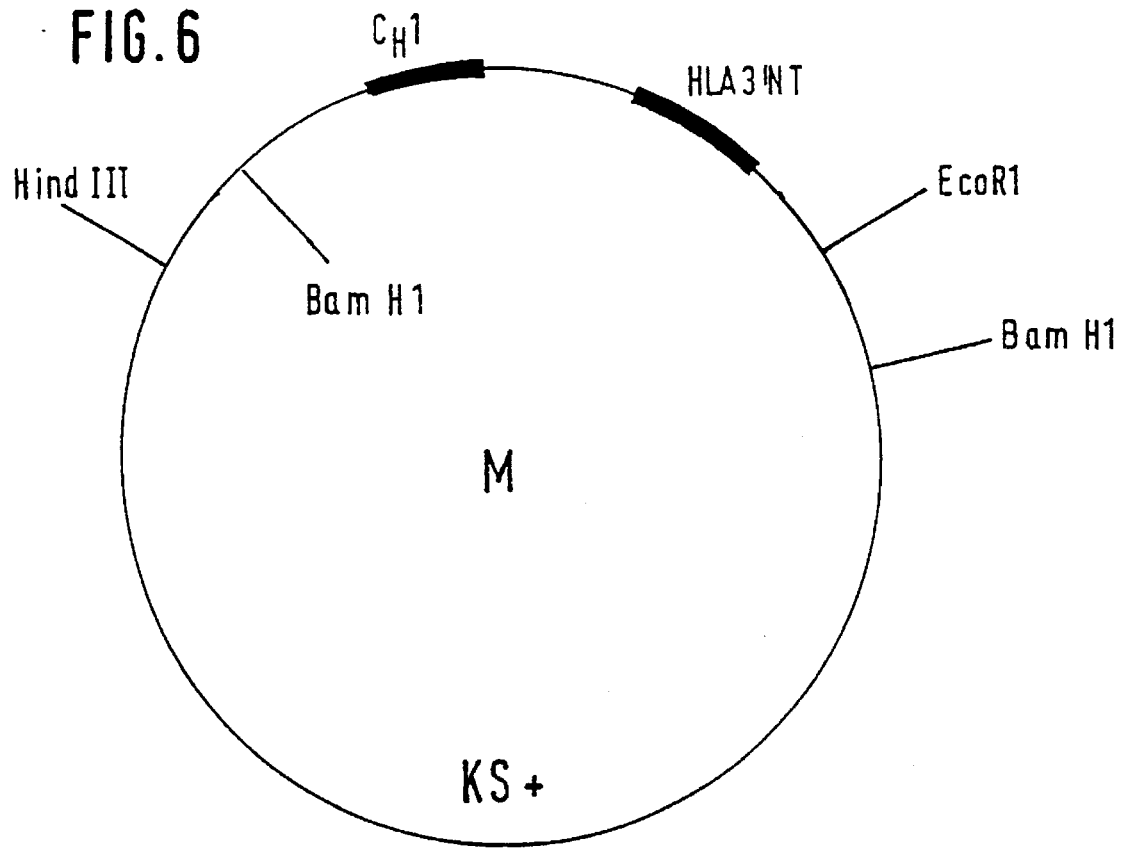
FIG. 6 depicts plasmid M containing the $C_H1$ exon and the 3' NT region of an HLA B27 gene.

Constructions which contain, on the one hand, only the $C_H$1 exon and a hinge exon (FIG. 5) and, on the other hand, the $C_H$1 exon and the 3'NT region of an HLAB27 gene (FIG. 6, fragment M in plasmid M) were prepared from this $IgG_3$ C gene as described in German Patent Application P 38 25 615.0.

Figure 7:
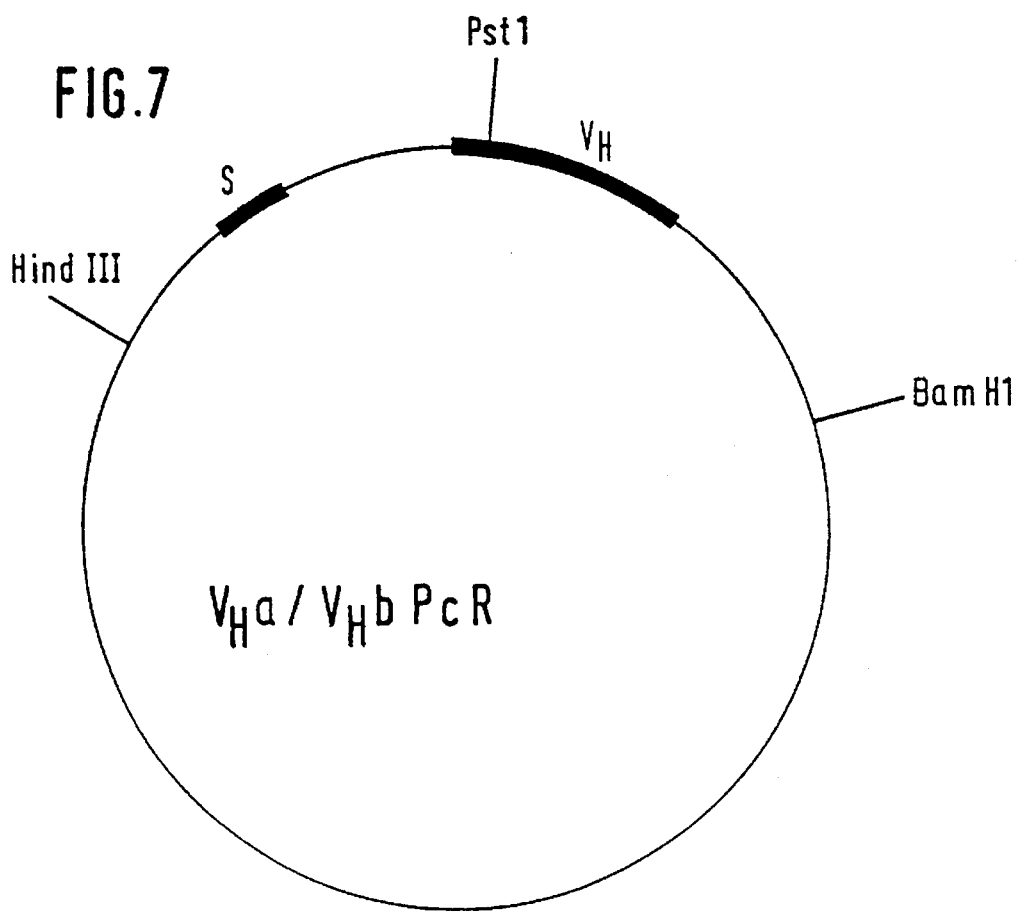
FIG. 7 depicts an M13 vector containing the $V_Ha$ and $V_Hb$ genes.
Figure 8:
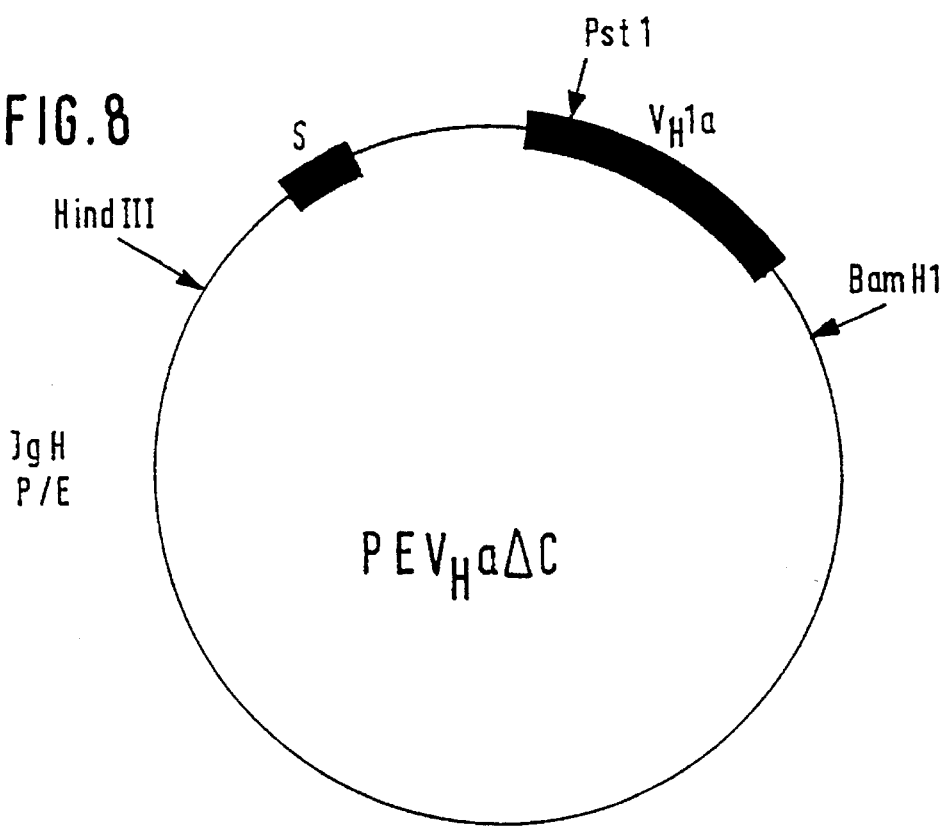
FIG. 8 depicts the plasmid $pEV_H$ a C containing the $V_Ha$ gene.

The $V_H$a and $V_H$b genes were amplified from mRNA of the hybrid clones a and b as described by Orlandi et al. (Proc. Natl. Acad. Sci. U.S.A. 86, (1989), 3833–3837) and cloned in an M13 vector ($V_H$a PCR and $V_H$b PCR) (FIG. 7). The $V_H$a gene was cloned as the HindIII-BamHI fragment into the eukaryotic expression vector $pEV_H$ (Simon et al., Nucl. Acids. Res. 16, (1988), 354) (FIG. 8). The result is the plasmid $pEV_H$ a C.

Figure 9:
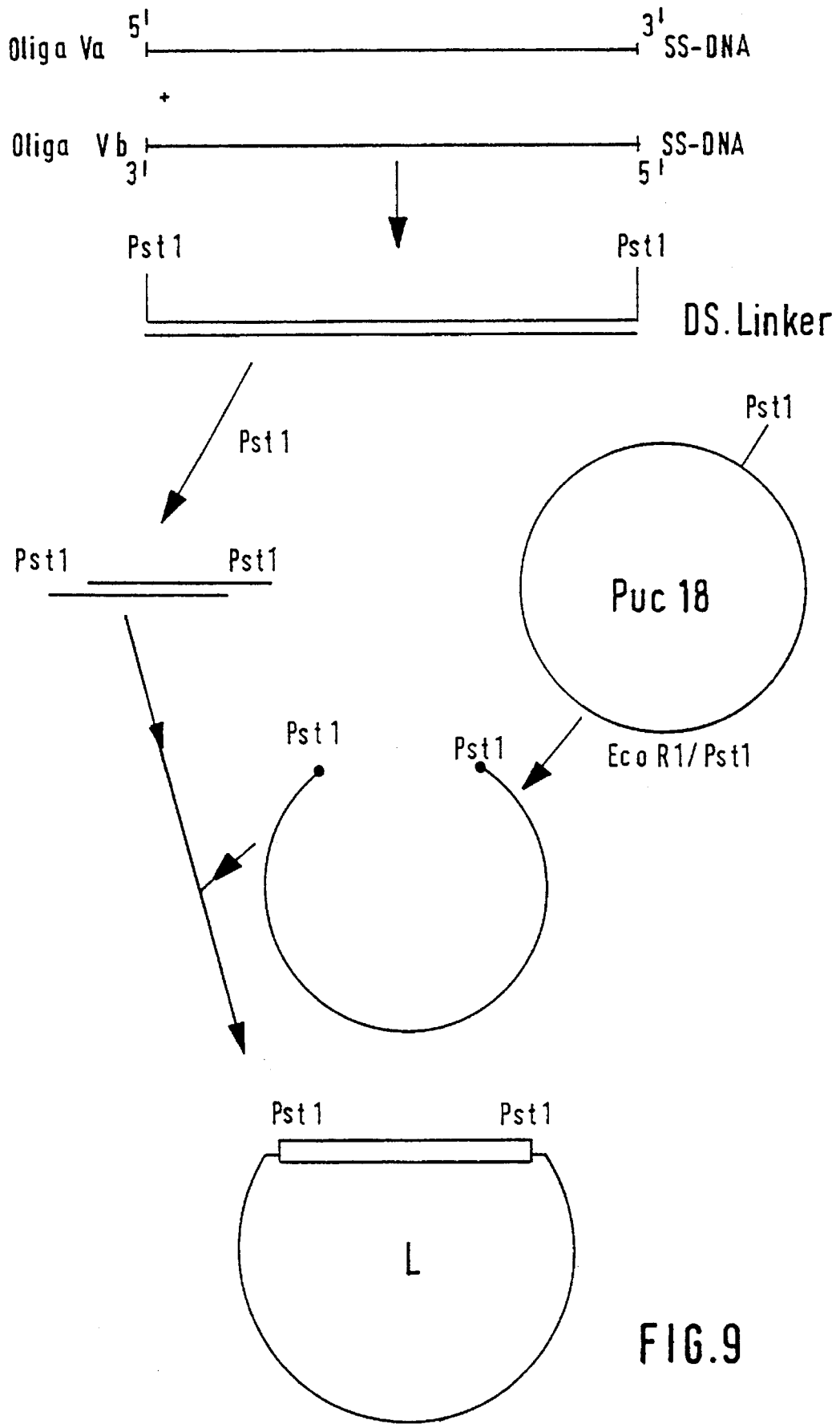
FIG. 9 depicts the construction of plasmid clone L.

The human IgG C gene subclone with the $C_H$1 and with one hinge exon (FIG. 5) contains a PstI cleavage site between $C_H$1 exon and hinge exon. The $V_H$ genes contain a PstI cleavage site at the 5' end. The linker oligonucleotide is designed such that it overlaps at the 5' end with the region of the PstI cleavage site on the $C_H$1+1H subfragment of the IgG C gene and at the 3' end with the PstI cleavage site of the $V_H$b gene. The linker oligonucleotide is cloned by means of its PstI cleavage sites into the PstI cleavage site of a PUC 18 plasmid (FIG. 9). The result is the plasmid clone L.

Figure 10:
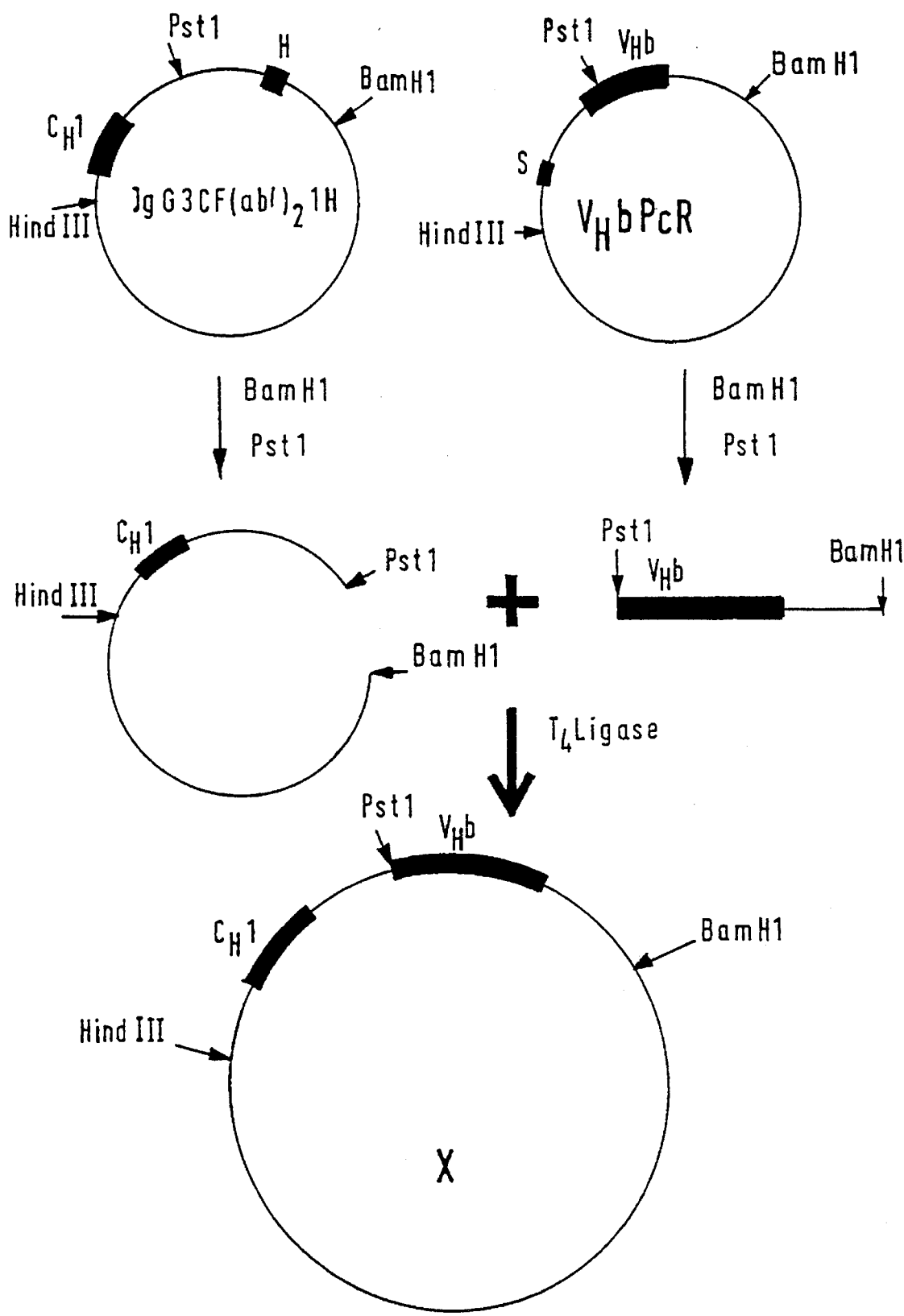
FIG. 10 depicts the construction of plasmid X.

The plasmid with the $IgG_3$ C gene subfragment with $C_H$1 exon and with a hinge exon is cleaved with PstI and BamHI and ligated to the $V_H$b gene fragment cut out of $V_H$b PCR as PstI-BamHI fragment (FIG. 10). The result is the plasmid X.

Figure 11:
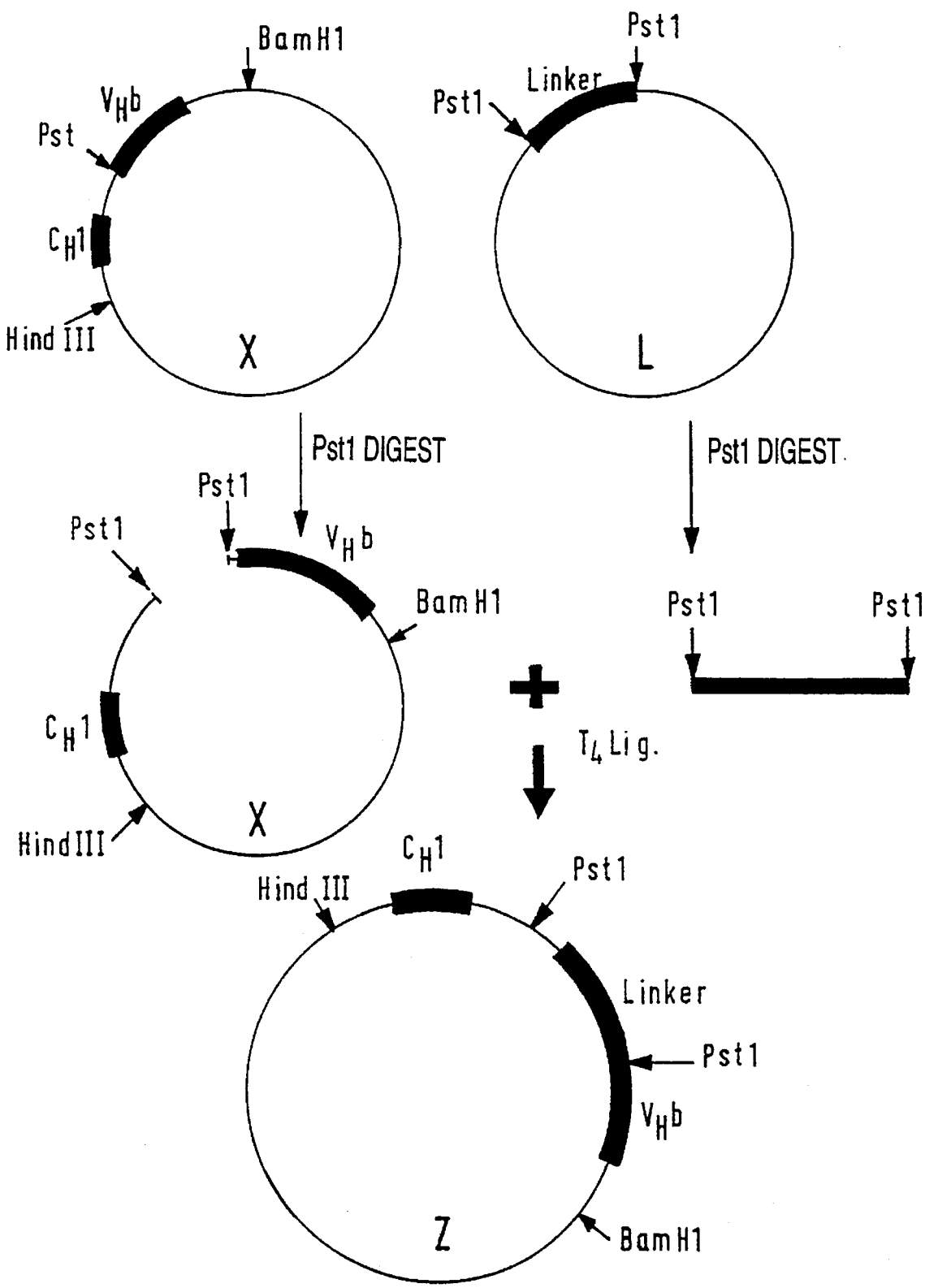
FIG. 11 depicts the construction of plasmid Z.

The plasmid X is cleaved with PstI and ligated to the linker fragment which has been cut out of the plasmid L likewise with PstI (FIG. 11). Nucleic acid sequence analysis is used to identify the clone Z in which the linker is cloned in correct orientation between $C_H$1 and $V_H$b without disturbing the intron/exon junction between intron 3 and linker exon and without disturbing the reading frame at the junction between linker and $V_H$b gene.

Figure 12:
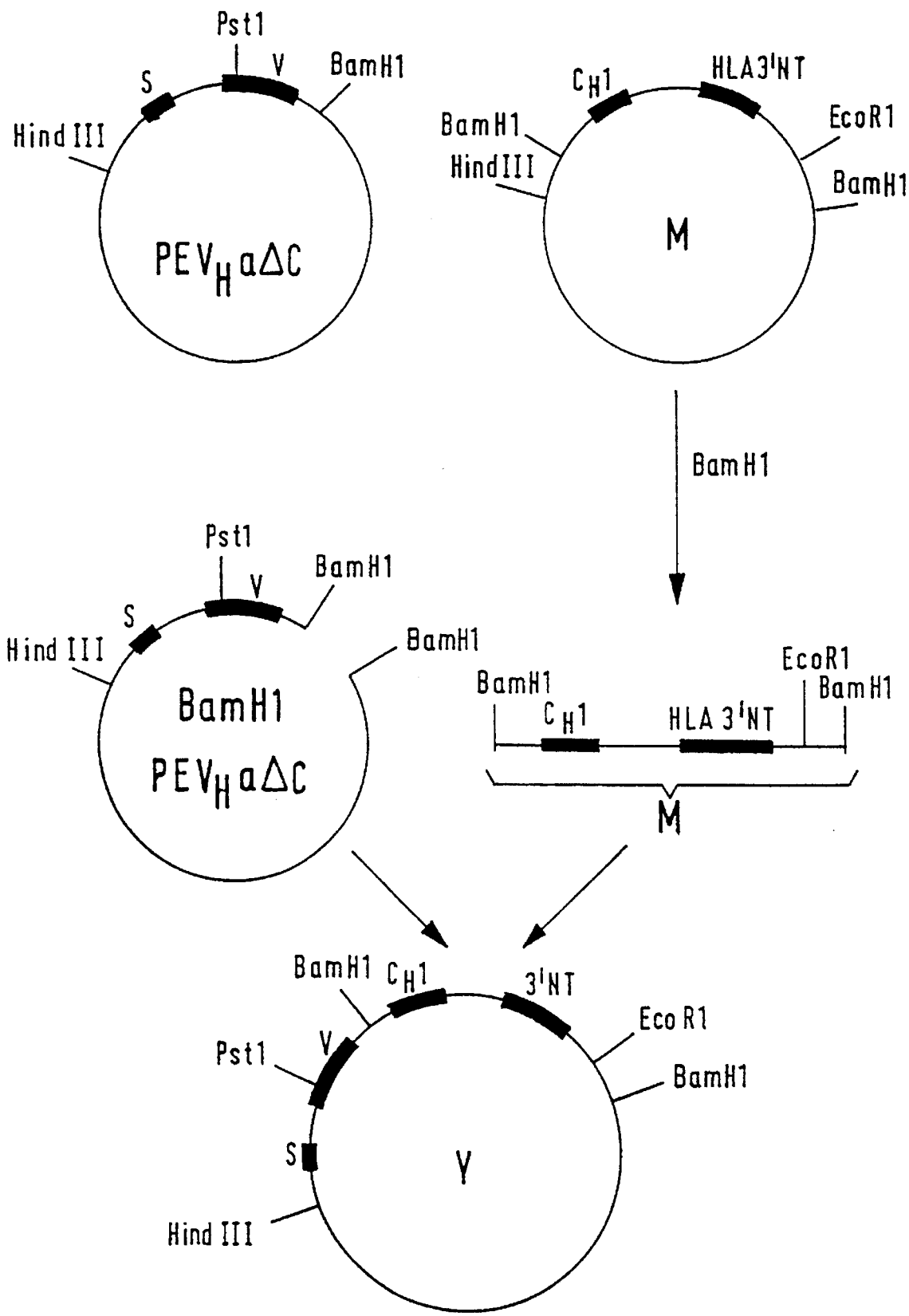
FIG. 12 depicts the construction of plasmid Y.

The plasmid pEVa C is cleaved with BamHI and ligated to the fragment M cut out of the plasmid M with BamHI. Restriction analysis is used to identify the clone Y which contains the fragment M in the correct orientation (FIG. 12).

Figure 13:
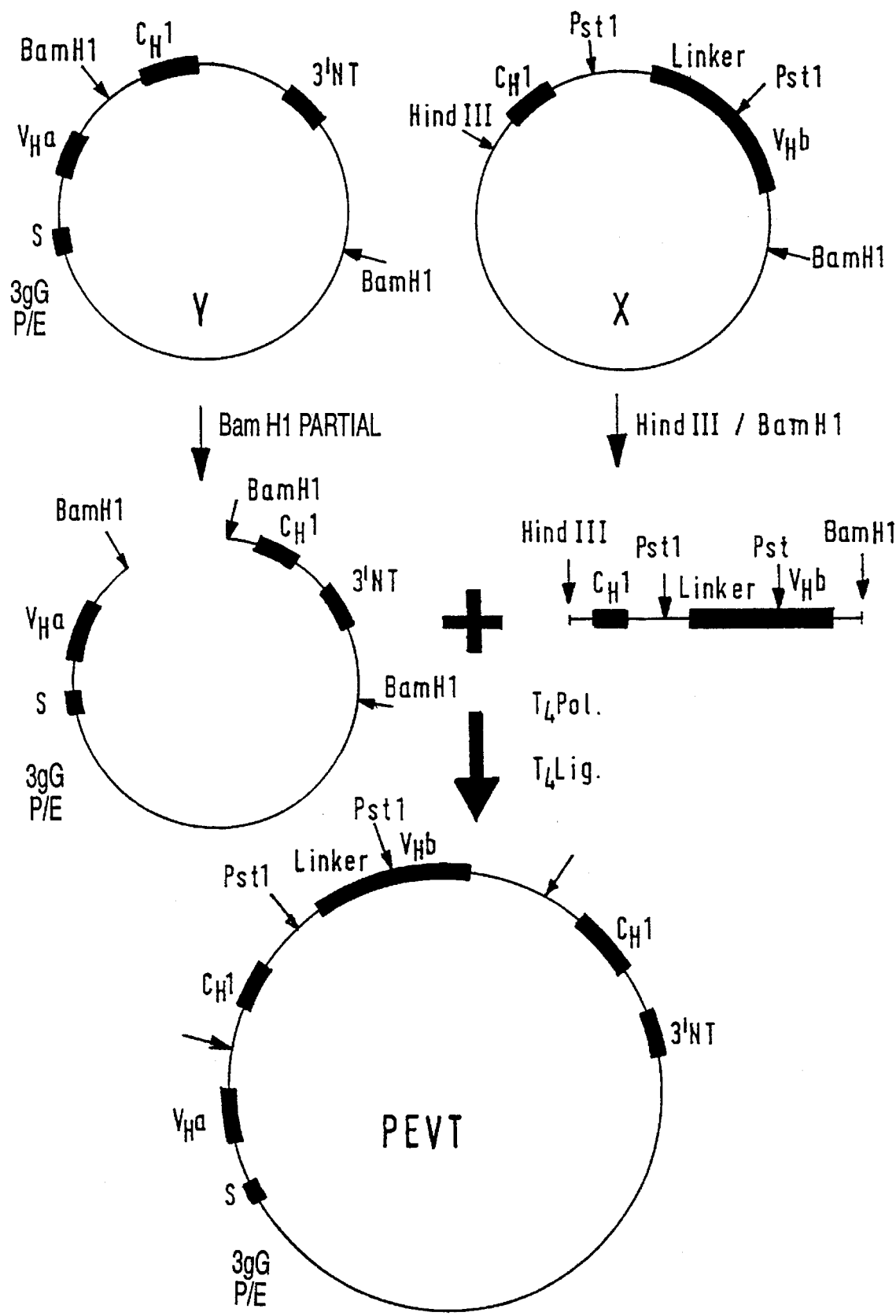
FIG. 13 depicts the construction of plasmid PEVT.

The plasmid Y is partially cleaved with BamHI and ligated to the fragment ($C_H$1-linker-$V_H$b) cut out of the plasmid X by HindIII and BamHI cleavage, after all the ends have been filled in. Nucleotide sequence analysis and restriction mapping are used to identify the plasmid clone PEVT which contains the fusion gene$V_H$a $C_H$1-linker-$V_H$b $C_H$1 with the correct orientation of all the exons (FIG. 13).

The plasmid PEVT is transfected together with plasmids which harbor the genes for the light chains of antibodies a and b into suitable eukaryotic expression cells in order to express the antibody a F (ab) antibody b F (ab) fusion protein.

EXAMPLE 3

Transfection of the light and heavy chain genes of two different MAbs (4 genes)

The isolation of immunoglobulin genes is described in German Patent Application P 39 09 799.4.

The genes cloned into vectors were transfected by electroporation after linearization of the vectors into X63Ag8.653 myeloma cells (H. Stopper et al., Biochem. Biophys. Acta 900 (1987), 38–44). The transfectomas which grew in selective media were tested for the production of bispecific monovalent MAbs in a specific RIA. This RIA comprised TAA adsorbed on a solid phase, onto which, after blockade of the non-specific sites by casein, the transfectoma supernatants to be assayed were placed. After DTPA or EDTA which were complexed with $^{90}Y$ or $^{99m}Tc$ had been added and the excess had been washed away, it was possible to detect those transfectomas which secreted bispecific monovalent anti-TAA×anti-EDTA MAbs by an increased radioactive signal on the solid phase.

Transfectoma 9 was stabilized by limited dilution cloning and expanded in cell culture. Cell culture supernatants were concentrated 10×, the MAb fraction was purified by protein A chromatography (P. L. Ey et al., Immunochemistry 15, (1978), 429), and the fraction containing the bispecific monovalent MAb was purified by anion exchange chromatography (J. Van Dijk et al., Int. J. Cancer 43, (1989), 344–349).

EXAMPLE 4

Biological effectivity

Purified protein containing the bispecific monovalent MAb (BW 431/26×BW 2050/174) was injected i.v. in 500

µg doses on days 0, 3, 5, 8, 10 and 12 into nude mice carrying human tumor xenografts (CoCa 4). 50 µCi of EDTA-Y90 were injected i.v. into each of the animals of day 27–30. A 2nd group of animals received on the same days 500 µg of MAb BW 431/26 in place of the bispecific MAb, and the EDTA-Y90 injections as described above.

A third tumor-carrying group received injections of PBS (as tumor-growth control) in place of the MAb and EDTA-Y90. Tumor growth was followed for 6 weeks. Injection of EDTA-Y90 resulted in significant inhibition of tumor growth in the group which received the bispecific monovalent MAb, whereas the animals injected with MAb BW 431/26 and treated with EDTA-Y90 showed no inhibition of tumor growth, compared with animals which received only PBS.

These data indicate the selective tumor-therapeutic efficacy of the bispecific monovalent MAb in combination with EDTA-Y90 as toxic principle.

Even more favorable tumor-therapeutic effects are obtained by the oligovalent/bispecific or oligospecific receptors because they remain longer on the tumor, because of the bivalent binding to TAA, and thus the ligand is likewise retained on the tumor for longer and in higher concentrations.

EXAMPLE 5

Optimization of the biological effectivity of bi- or oligospecific macromolecules by increasing the avidity of the anti-chelate arm A crucial factor which influences the efficient attachment of the hydrophilic chelate undergoing extracellular distribution to the anti-chelate arm of the oligospecific macromolecule is the avidity of this arm for the chelate. The avidities of monoclonal antibodies for their corresponding epitopes are in the range $10^5$–$10^{11}$/mol. Since these binding strengths are possibly insufficient to localize on the tumor the mass of chelate necessary for efficient radioimmunotherapy, in the following example the extremely strong interaction of the fos-leucine-zipper peptide (fos-peptide) with the jun-leucine-zipper peptide (jun-peptide) (Erin K. O'Shera et al., Science, 245, 1989) was used to immobilize the chelate as firmly as possible on the anti-chelate arm. It is necessary, in order to be able to utilize this strong fos-jun interaction, preferably to link the fos-peptide covalently to the chelate (DTPA). It is possible for this purpose to react in a first step isothiocyanatobenzyl-DTPA with hydrazine (or a diaminoalkane). The DTPA-benzylthiocarbazide produced in this way can be reacted, in a 2nd step, with N-(gamma-maleimidobutyryloxy)succinimide or an analog to give DTPA-benzyl-(gamma-maleimidobutyryl)thiocarbazide. Then, in a 3rd step, this compound is linked to the fos-peptide which has been extended by glycine-glycine-cysteine (FIG. 1) via the free SH group of the amino-terminal cysteine. The fos-peptide-DTPA conjugate produced in this way is complexed in a 4th step with yttrium chloride. The fos-peptide-DTPA-Y conjugate complex produced in this way can then be used for in vivo addition onto the jun-peptide arm of the bi- or oligospecific macromolecule. The synthesis of the example outlined above is described in detail hereinafter:

A) Preparation of the fos-EDTA-Y conjugate complex

Step 1:

Synthesis of EDTA-benzylthiocarbazide

Isothiocyanatobenzyl-EDTA (SCN-Bn-EDTA) (30 mg, 54 µmol) was stirred in 10% (v/v) aqueous hydrazine for 1 h. The solvent was then removed under high vacuum, and the residue was dried over phosphorus pentoxide under high vacuum and finally freeze-dried. The product was neutralized with DOWEX WX 2 ($H^+$ form) and again freeze-dried (yield 28 mg).

Step 2:

Synthesis of EDTA-benzyl(gamma-maleimidobutyryl)thiocarbazide

The EDTA-benzylthiocarbazide prepared in step 1 (20 mg; 34 µmol) and N-(gamma-maleimidobutyryloxy)succinimide (8 mg, 29 µmol=0.9 equiv.) were stirred in anhydrous dimethylformamide for 1 h. The mixture was then evaporated to dryness, and the residue was dried under high vacuum.

Step 3:

Coupling of the EDTA-benzyl(gamma-maleimidobutyryl)thiocarbazide to the amino-terminal cysteine in the fos-peptide A solution of the fos-peptide (4.8 mg, 1 µmol) (see step 3.1) in phosphate-buffered saline (2 ml) was mixed with a suspension of the product mixture obtained as in step 2 (4 mg) in dimethylformamide (400 µl) and incubated at room temperature for 1 h. The reaction mixture was then subjected to gel filtration on a Sephadex G15 column in phosphate-buffered saline. The protein-containing eluate was collected and preserved at –30° C. (yield 4.2 mg).

Step 3.1:

Amino acid sequence of the fos-peptide (I I) with N-terminal GGC extension.

Ac-CGGyLTDTLQAETDQLEDKKSALQTE-IANLLKEKEKLEFILAAYy The letters represent the following amino acids: A=alanine, C=cysteine, D=aspartic acid, E=glutamic acid, G=glycine, I=isoleucine, K=lysine, L=leucine, M=methionine, N=asparagine, Q=glutamine, R=arginine, S=serine, T=threonine, V=valine, Y=tyrosine.

The oligopeptide was synthesized using an automatic peptide synthesizer (Applied Biosystems Model 430A) by the Merrifield solid-phase method (Stewart and Young, Solid Phase Synthesis, Pierce Chemical Company, 2nd edition, Rockford Ill.) with the tert-butyloxycarbonyl protective group. The oligopeptides were cleaved off the phenylacetamidomethyl-polystyrene support. After elimination of the protective groups (Tom et al., 1983, J. Am. Chem. Soc. 105, 6442-6455) the oligopeptides were purified by reversed phase chromatography (PepRPC column, Pharmacia) as described by Rivier et al. (J. Chromatography 288, 303–328, 1984).

Step 4:

Preparation of a fos-peptide-EDTA-yttrium chelate with a fos-peptide-EDTA conjugate prepared as in step 3

The fos-peptide-EDTA conjugate prepared as in step 3 (4.2 mg) was dialysed against isotonic saline/0.1M sodium citrate, pH 7.0, in a dialysis tube with an exclusion limit of m.w. 1,000 (Spectrum), and was mixed with 6 mg of yttrium chloride which were dissolved in 3 ml of isotonic saline/0.1M sodium citrate, pH 7.0. After 1 h, back-dialysis against phosphate-buffered saline was carried out, and the chelate solution was preserved at –30° C. The fos-peptide-EDTA-Yttrium chelate described in the above example is then used as ligand in order to bind with high avidity to the jun-peptide arm of the bi- or oligospecific macromolecule. The construction of a bispecific macromolecule particularly suitable for this interaction is described in the following example.

B) Construction of the MAb-jun fusion molecule

The techniques used here were taken, unless otherwise indicated, from Maniatis et al. (Laboratory Manual EMBL (1982), Heidelberg), and Sambrook (Molecular Cloning: A Laboratory Manual).

Figure 14:
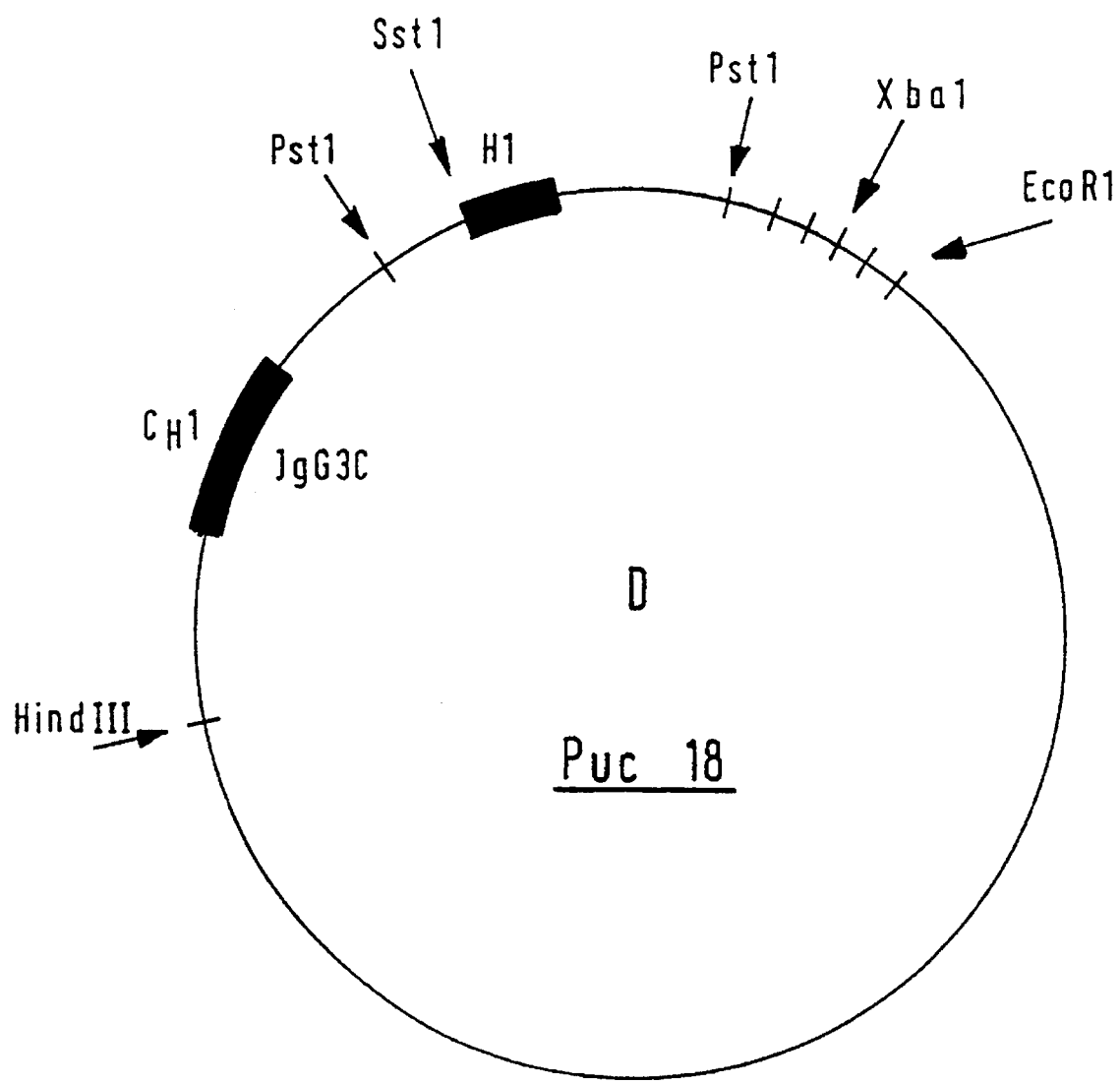
FIG. 14 depicts plasmid D containing the CH1 exon and the first hinge oxon of the IgG3 C gone.

Step 1:

A human IgG3 C gene was isolated from a human gene bank in EMBL 3 phages (A. M. Frischauf et al., J. Mol. Biol. 170, 827–842, 1983 and G. H. A. Seemann et al., The EMBO Journal 5, 547–552, 1986). A construction (D) which contains only the CH1 exon and the first hinge exon of the IgG3 C gene (FIG. 14) was prepared from this IgG3 C gene as described in German Patent Application P 3825615.0.

Figure 15:
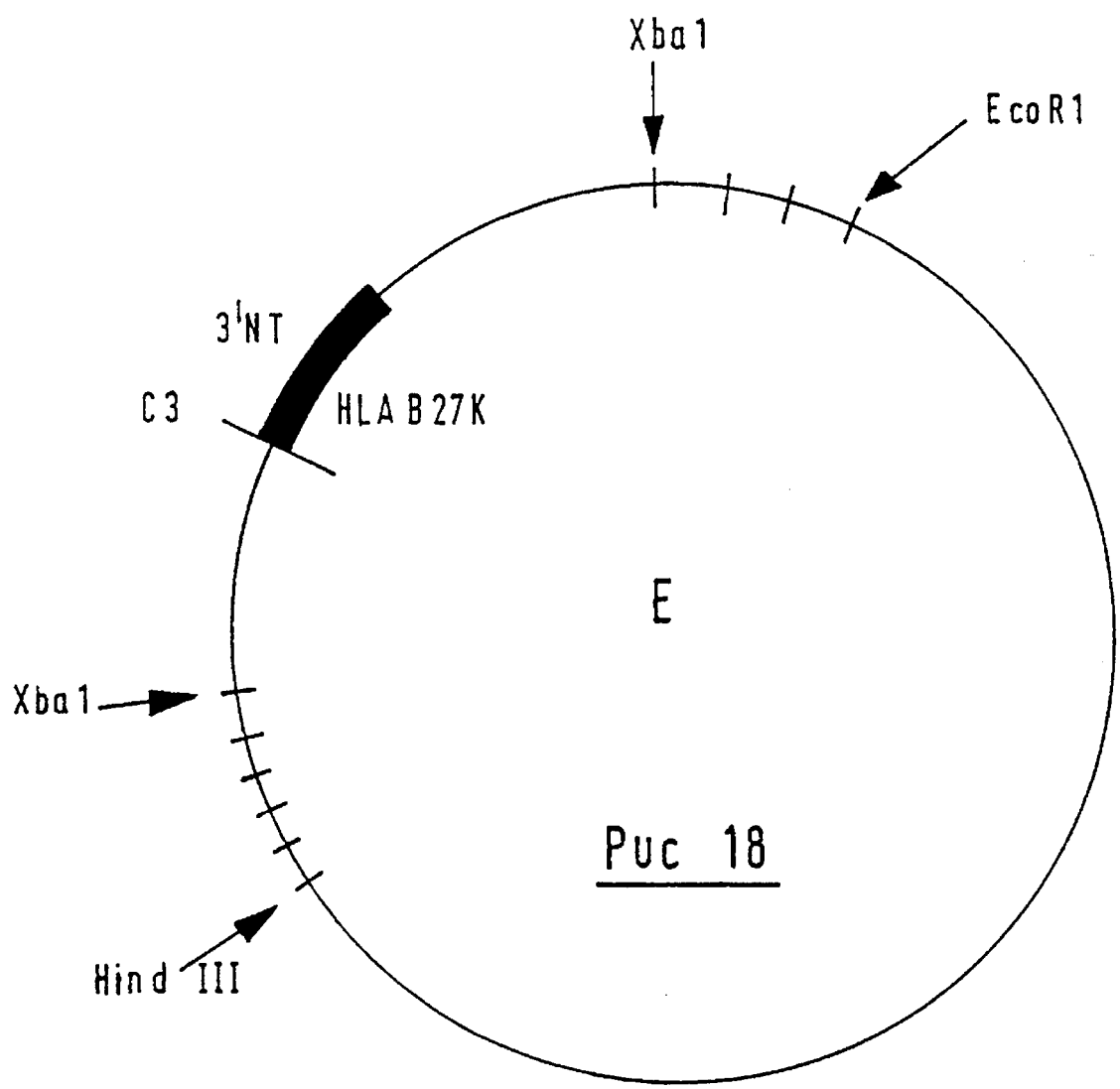
FIG. 15 depicts plasmid E containing the C3 exon and the 3' NT region of the HLA B27k gene.

A human HLA B27k gene was isolated from the same gene bank as likewise described in German Patent Application P 3825615.0. A construct (E) which contains only the C3 exon and the 3' NT region of the HLAB27k gene (FIG. 15) was prepared from this HLAB27k gene.

Figure 16:
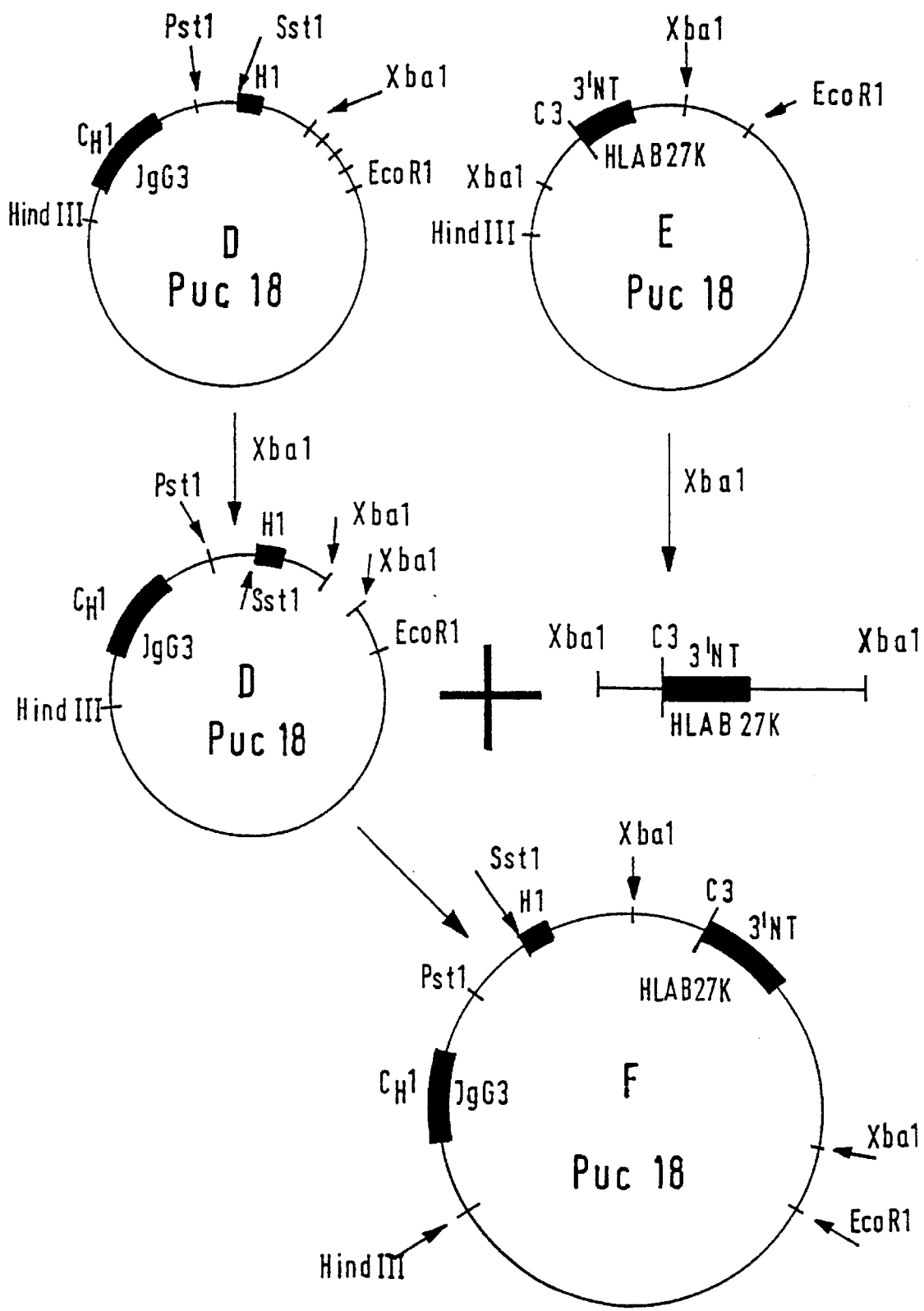
FIG. 16 depicts the construction of plasmid F.

Step 2:

The C1 exon and the 3' NT region of the HLAB27k gene were cut out of the plasmid E with XbaI, and the fragment was isolated and cloned into the XbaI cleavage site of the construct D. Restriction analysis and nucleic acid sequence analysis were used to identify the clone F which contains the C3 exon and the 3' NT region of the BLAB27k gene in the correct 5'-3' orientation 3' from the IgG3 C gene fragment (FIG. 16).

Figure 17:
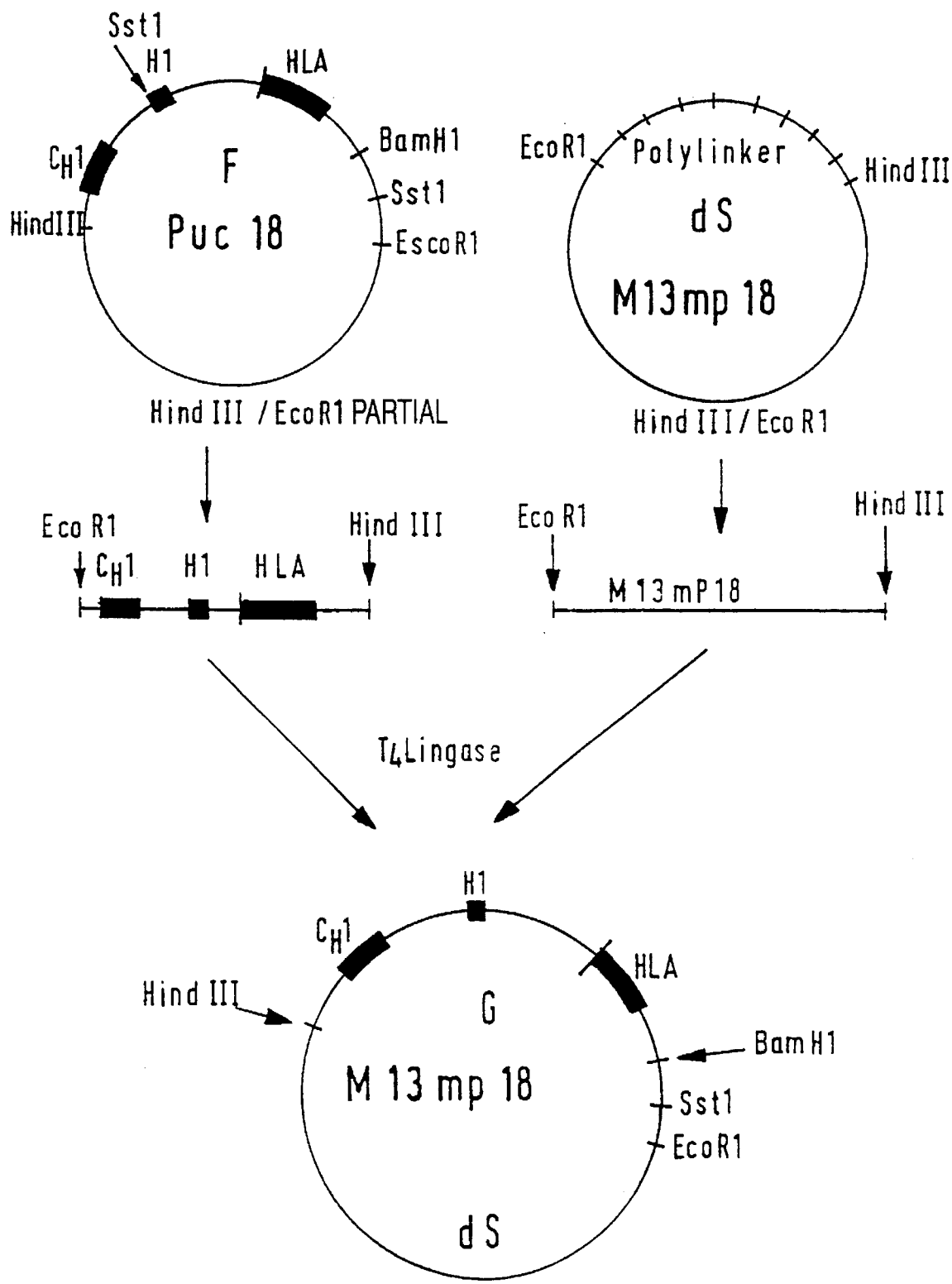
FIG. 17 depicts the construction of plasmid G.

Step 3:

The insert of the clone F is cut out of the plasmid using the endonucleases HindIII and EcoRI and cloned between the HindIII and EcoRI cleavage sites of an M13mp18 double-stranded (DS) phage. The phage clone G which contains the antibody/HLA fusion gene fragment is isolated (FIG. 17).

Figure 18:
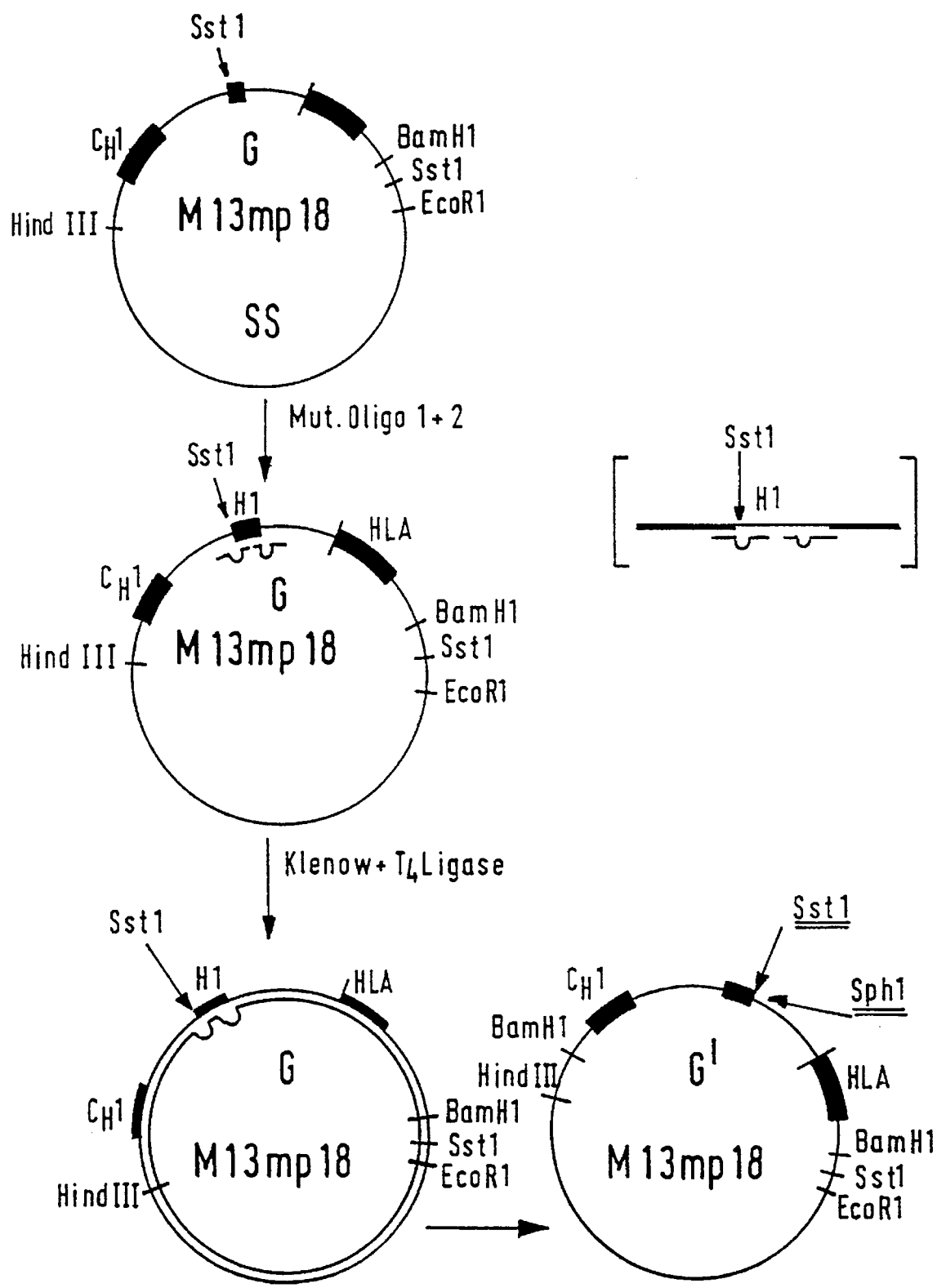
FIG. 18 depicts plasmid G' containing a SstI and a SphI restriction cleavage site at the 3'-end of the hinge exon and without a SstI restriction cleavage site at the 5' end of the hinge exon.

Step 4:

Uracil single strands are prepared from the phage clone G by the method of T. A. Kunkel, 1985, Proc. Natl. Acad. Science, U.S.A., 82, 488–492. The single-stranded phages were hybridized with the mutagenic oligonucleotides 1 and 2 (Tab. 6), and the gaps between the oligonucleotides were closed with Klenow DNA polymerase and T4 ligase. After transformation into *E. coli*, restriction analysis and nucleic acid sequence analysis were used to identify a phage clone (G') in which the SstI restriction cleavage site at the 5' end of the hinge exon had been deleted. At the same time, a SstI and a SphI restriction cleavage site were introduced at the 3' end of the hinge exon (FIG. 18). To delete the SstI cleavage site, the third base of the 2nd codon of the hinge exon was converted from C into G, and to introduce the SstI and SphI cleavage sites, the bases 5'GAGCTCGGGGCA3' were introduced between the 15th and 16th codon of the hinge exon (Tab. 7).

Step 5:

Double-stranded DNA of the phage clone G' is cleaved completely with SphI and partially with SstI. The synthetic oligonucleotides Jun I and Jun II (Tab. 8) are combined to give a double-stranded DNA fragment which contains at each of its ends a cut SphI and SstI restriction cleavage site and codes for a peptide which contains the Jun leucine zipper (O'Shea et al., Science, 245, 646–648, 1989).

Figure 19:
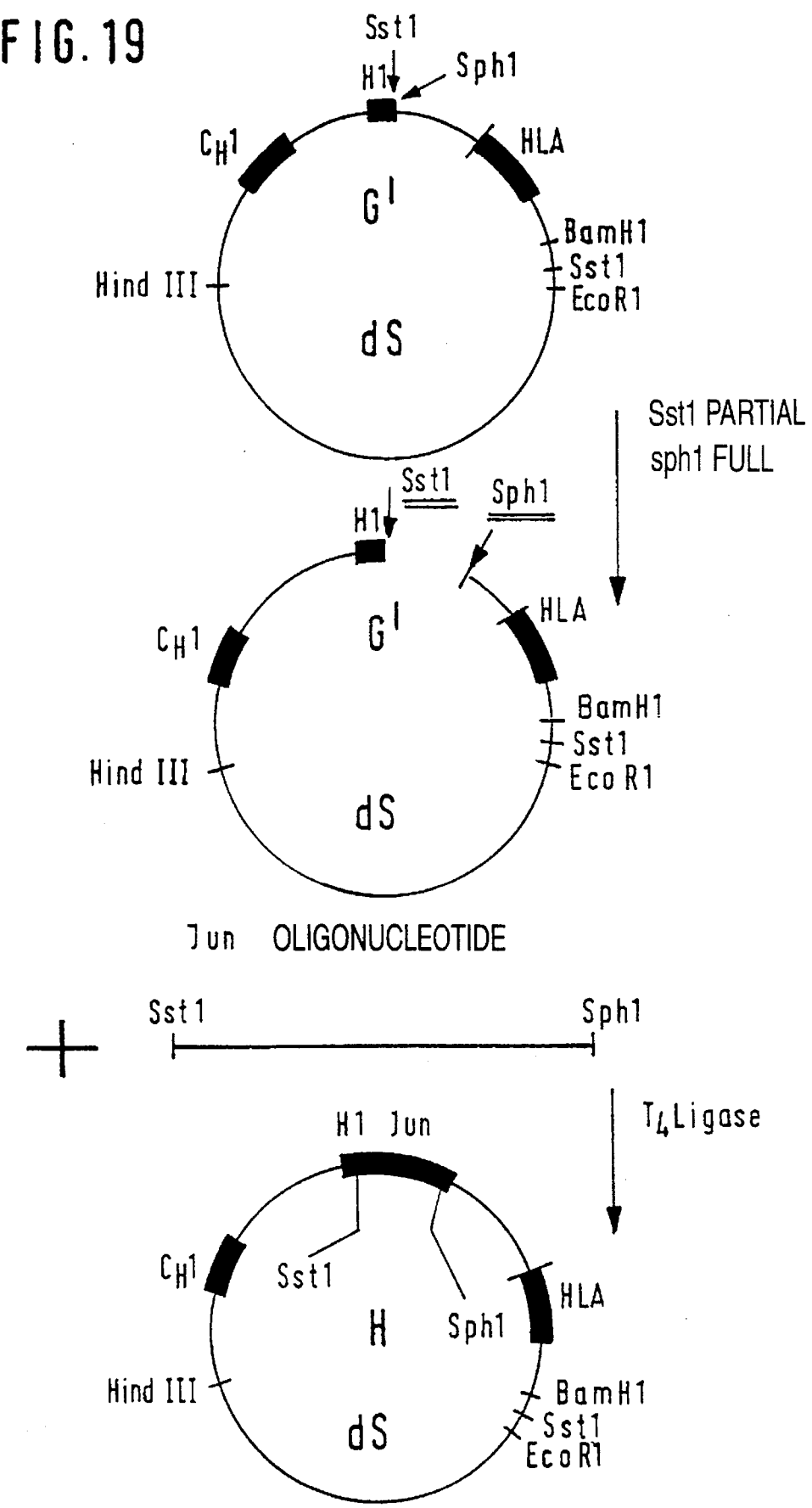
FIG. 19 depicts the construction of plasmid H.

The double-stranded DNA fragment is cloned into the SstI and SphI restriction cleavage sites of the F' phage clone, and the phage clone H which contains a gene construct in which the sequence for the Jun zipper peptide is inserted in the hinge exon is identified (FIG. 19).

Figure 20:
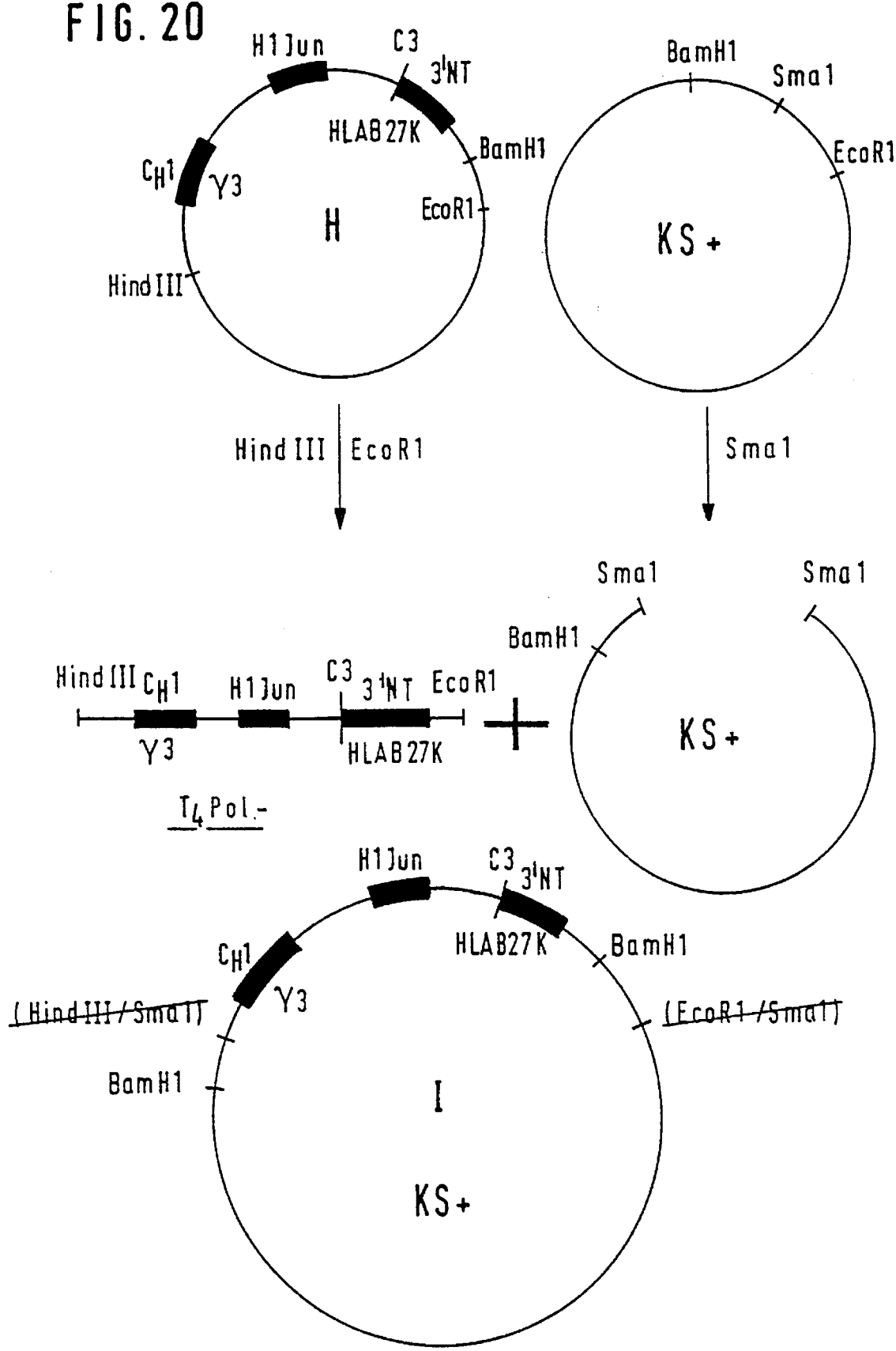
FIG. 20 depicts the construction of plasmid I.

Step 6:

The insert of the DS phage H was cut out with the restriction endonucleases HindIII and EcoRI, the ends were filled in with T4 polymerase and cloned into an SmaI-cleaved KsF vector (Stratagene, 11099 North Torrey Pines Road, La Jolla Calif. 92037). Plasmid clone I which contains the antibody/Jun/HLA fusion gene in the orientation (FIG. 20) in which it is flanked on both sides by a BamHI cleavage site was identified.

Figure 21:
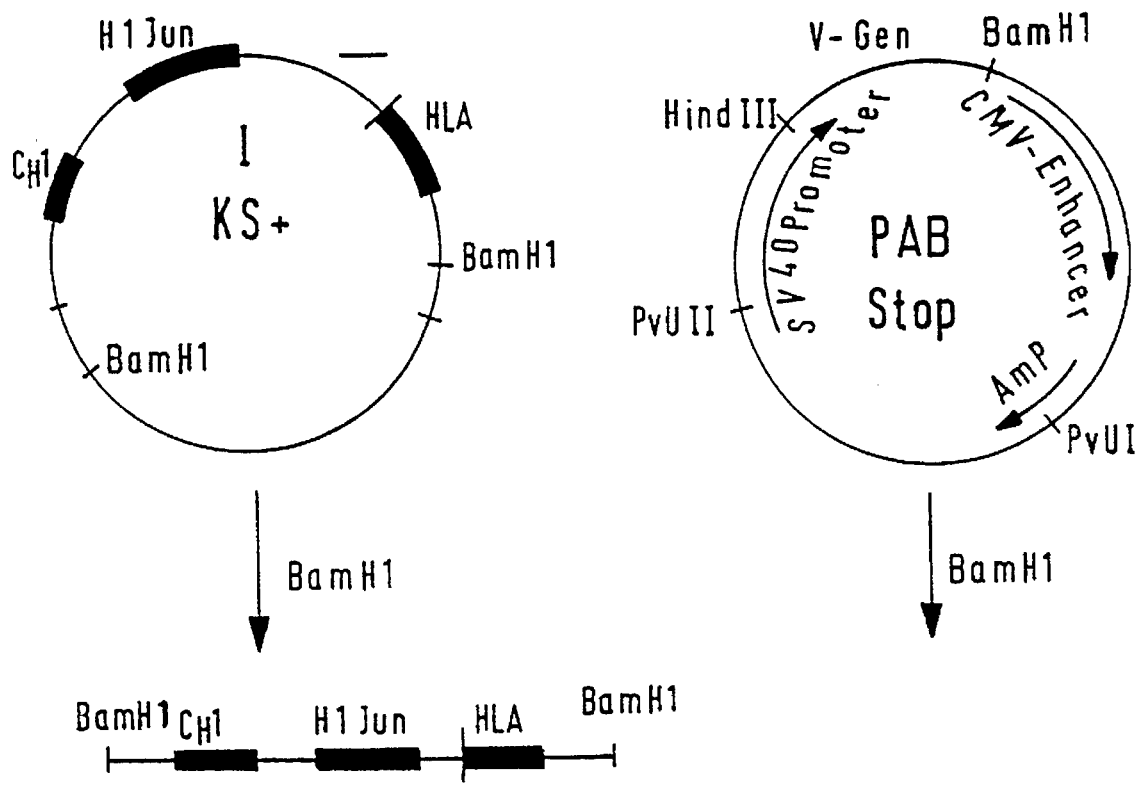
FIG. 21 depicts the construction of plasmid K.
Figure 21:
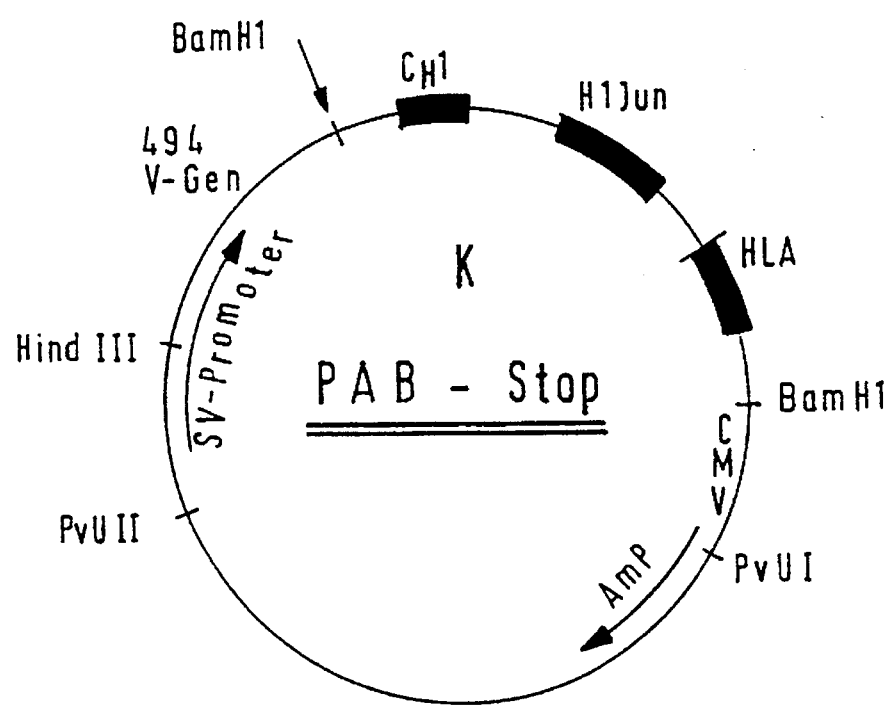

Step 7:

The antibody/Jun/HLA fusion gene was cut out of the KS clone I with BamHI and cloned into the expression plasmid pABStop (Behringwerke AG) which contains a specific functional immunoglobulin V gene. The specific V gene was obtained as described in Patent Application P 3909799.4. The expression plasmid K which contains the antibody/Jun/HLA fusion gene construct in the correct orientation downstream of the $V_H$ gene was identified (FIG. 21).

Cotransformation of the plasmid K with a plasmid which contains the gene for the light chain of the specific MAb, and a plasmid which carries a resistance gene, leads to expression of a specific antibody $F(ab')_2$ fragment which contains in the hinge region two Jun zipper peptides, with the Jun zipper peptide being modified in such a way that there is no longer any homodimer (Jun/Jun) formation.

EXAMPLE 6

Optimization of the amount of bi- or oligospecific receptor on the tumor and minimization thereof in the blood and normal tissues Scientific investigations by others have shown that penetration of solid tumors by macromolecules >50 kDa takes place slowly, and usually only the edge region or a few areas in the tumor are reached. These investigations are based on experiments which comprise a single injection of small amounts of macromolecules. In contrast thereto, we have found that substantial penetration of the entire tumor mass in nude mouse xenografts is possible by a repetitive i.v. injection of large amounts of bi- or oligospecific receptors (10×250 μg receptor/mouse for 10 days). Furthermore, because of their specific binding to TAA, the bi- or oligospecific receptors remain attached for long periods (>20 days) in large amounts on the tumor cell membrane and in the tumor interstitium. These results were obtained using the indirect alkaline phosphatase technique on cryopreserved thin sections of human colonic and pancreatic tumor xenografts.

During this time (after only 10 days) the bi- or oligospecific receptor molecules had already been eliminated from the TAA-negative normal tissues and the blood by degradation and excretion. In order to shorten this elimination period, an anti-idiotype MAb (anti Id) which reacts only with the anti-TAA arm of unbound bi- or oligospecific receptor molecules was injected i.v. (1×50 μg of anti Id) 24 hours after completion of the ten injections of bi- or oligospecific receptors. This single injection speeded up the elimination of the unbound bi- or oligospecific receptor molecules from the blood and increased the metabolism rate in liver and spleen.

It is possible on the basis of this manipulation to inject the chelate (EDTA-Y90) only 4 days after completion of the phase of penetration and binding of the bi- or oligospecific receptor. The following treatment regimen (for nude mice) is derived from these investigations a) day 1–10, i.v. injection of 1×250 μg of bi- or oligospecific receptor each time b) day 11, i.v. injection of 1×50 μg of anti Id c) day 14, i.v. injection of a therapeutic dose of EDTA-Y90.

On the basis of comparative immunoscintigraphic data in nude mice and tumor patients, this regimen ought to be suitable for tumor therapy in humans too. However, the amounts to be injected in the human system are in a different range of magnitude. 10×5–10 g of bispecific receptor, 1×1 g of anti Id. Injection of the anti Id is not indispensable for therapy.

Annex 1a

Quantitative inhibition ELISA for MAbs by DTPA or EDTA complexes

Material: divisible 96-well polystyrene microtiter plates (U shape) type B, from Nunc, No. 4-60445

1) 50 µl of Y-benzyl-DTPA-HSA 19 conjugate with a concentration of 1 µg of conjugate per ml of PBS, pH 7.2, are pipetted into each well and incubated at room temperature (RT) overnight.
2) The supernatant is removed by aspiration and washed 3×with 0.05M tris citrate buffer, pH 7.4, (wash solution 1); (1×wash=introduce 250 µl of wash solution per well, leave to stand for 2 min and remove by aspiration).
3) If the microtiter plate is not required immediately, it is left to stand (with the opening underneath) on cellulose at RT overnight. The plate is then sealed in films with drying cartridges (from Gaplast, Postfach 529, 8100 Garmisch-Partenkirchen). The plates can be kept at +4° C. for at least 8 weeks under these conditions.
4) 250 µl of blocking solution are applied to each well and incubated at 37° C. for 30 min.
5) Preincubation of the diluted hybridoma supernatant with the competitor is carried out during the blocking (see Annex 1b).
6) 50 µl of the appropriately prediluted and preincubated hybridoma supernatants to be tested are applied to each well and incubated at RT for 30 min.
7) Washing 3×with wash solution 2 is subsequently carried out.
8) Subsequently 50 µl of goat anti-mouse $IgG_1$ antibodies which are labeled with alkaline phosphatase and have been diluted 1:500 in blocking solution are applied to each well and incubated at RT for 30 min.
9) Then washing 3×with wash solution for Enzygnost is carried out.
10) Subsequently 50 µl of 0.1 mMNADP are added.
11) Incubation at RT is then carried out for 30 min.
12) During the incubation with NADP, the amplification system is made up as follows: per plate 2 parts of INT and 1 part of PBS, pH 7.2, are mixed and 1 part of diaphorase and 1 part of ADH are pipetted in.
13) 50 µl of this system are placed in each well.
14) When there is a distinct change in color from transparent to red the reaction is stopped with 100 µl of a 0.1N $H_2SO_4$ solution per well.
15) The extinctions are measured at 492 nm in a TITERTEK® MULTISCAN. 50 µl of NADP with 50 µl of solution and 1200 µl of 0.1N $H_2SO_4$ are employed as blank.

NADP—Sigma order No. N-0505
INT—Sigma order No. I-8377
ADH—Sigma order No. A-3263
DIAPHORASE—Sigma order No. D-2381

Wash solution 2—Behring, order No. OSEW96 contains Tween/PBS
Blocking solution:
PBS, pH 7.2, is made 3% strength in casein by adding casein and stirring for 30 minutes, and is adjusted to pH 7.4. Particles are then removed by centrifugation at 4,000 rpm for 10'.
Diluted goat anti-mouse $IgG_1$ antibodies labeled with alkaline phosphatase (from Southern Biotechnology Associates, Cat. No. 1080-04).
Preparation of 0.1 mMNADP:
Dissolve 7.65 mg of NADP in 100 ml of 20 mM tris, 0.1 mM $MgSO_4$, pH 9.5; this solution can be stored at −20° C. for several months.
Preparation of INT (P-IODONITROTETRAZOLIUM Violet):
Dissolve 2.5 mg/ml of 30% ethanol in an ultrasonic bath; always make up fresh.
Preparation of diaphorase:
1 mg of diaphorase/ml of PBS, pH 7.2, is stored in portions at −20° C.
Preparation of alcohol dehydrogenase:
0.5 mg of ADH/ml of PBS, pH 7.2, are stored in portions at −20° C.

Annex 1b

Preincubation of the hybridoma supernatant with the competitor

The mouse IgG concentration in hybridoma supernatants can be determined using commercially available quantitative ELISA systems and is state of the art.
On the basis of the ELISA concentration determination, the hybridoma supernatants are diluted to 1.25 µg/ml in PBS without $Ca^{++}$ and $Mg^{++}$.
Conversion from gram into mol:
50,000 g–1 mol of MAb
$1.25 \times 10^{-6}$ g–xmol
1.25 µg=x=$8.33 \times 10^{-2}$ mol
In order to have a 1+1 ratio of MAb and inhibitor, 10 µl of inhibitor with a concentration of $8.33 \times 10^{-12}$ mol/200 µl, which is increased by a factor of 5, were added to 50 µl of hybridoma supernatant with a concentration of $8.33 \times 10^{-12}$ mol/ml.
The hybridoma supernatant is incubated with 100,000-fold, 50,000-fold, 10,000-fold, 5,000-fold, 1,000-fold and 100-fold excess of competitor at RT for 30'. 50 µl of this are pipetted into the ELISA (see Annex 1a, no. 6).

Annex 1c

Production of the DTPA and EDTA complexes

The complexing constant of DTPA or EDTA to the metal ions depicted in Table I is extremely high so that complete saturation has to be expected on equimolar mixing of DTPA or EDTA with these metal ions. For this reason, the corresponding metal ions were incubated in a 3-fold molar excess with the DTPA or EDTA. As an example, 170 µl of a 10 mM cadmium sulfate solution in double-distilled water (see Annex 1d) were incubated with 30 µl of a 0.028 molar DTPA stock solution in double-distilled water at RT for 5'. Mixing 10 µl of this competitor solution with the hybridoma supernatant leads to a 100,000-fold excess of competitor over the MAb contained in the hybridoma supernatant. Lower competitor to MAb ratios were achieved by diluting the competitor solution in the particular salt ion solution appropriately for the desired molar excess (see Annex 1b).

Annex 1d

Source and relevant physicochemical parameters of the metal ions employed

Molar excess of competitor which leads to 50% inhibition of the binding to the solid-phase antigen.

| MAb No. | DTPA-Y | DTPA | DTPA-Mn | DTPA-Cd | DTPA-Zn | DTPA-Cn |
|---|---|---|---|---|---|---|
| 2050/174 | $10^4$ | $10^3$ | $10^2$ | $10^2$ | $5 \times 10^3$ | $5 \times 10^3$ |
| 2050/531 | $5 \times 10^4$ | $10^3$ | $10^2$ | $10^2$ | $5 \times 10^3$ | $5 \times 10^3$ |
| 2050/532 | $5 \times 10^4$ | $10^3$ | $10^2$ | $10^2$ | $5 \times 10^3$ | $5 \times 10^3$ |
| 2050/534 | $5 \times 10^4$ | $10^3$ | $10^2$ | $10^2$ | $5 \times 10^3$ | $5 \times 10^3$ |
| 2050/535 | $10^4$ | $10^3$ | $10^2$ | $10^2$ | $10^3$ | $10^3$ |

| MAb No. | DTPA-Pb | 1,2-Diamino-ethane | Trans-aconitic acid | | | |
|---|---|---|---|---|---|---|
| 2050/174 | $10^3$ | no inhibition up to $10^5$ | no inhibition up to $10^5$ | $10^2$ | $10^3$ | $10^3$ |
| 2050/531 | $5 \times 10^3$ | no inhibition up to $10^5$ | no inhibition up to $10^5$ | $10^3$ | $10^3$ | $10^3$ |
| 2050/532 | $5 \times 10^3$ | no inhibition up to $10^5$ | no inhibition up to $10^5$ | $10^2$ | $10^3$ | $10^3$ |
| 2050/534 | $5 \times 10^3$ | no inhibition up to $10^5$ | no inhibition up to $10^5$ | $10^2$ | $10^3$ | $10^2$ |
| 2050/535 | $10^3$ | no inhibition up to $10^5$ | no inhibition up to $10^5$ | $10^2$ | $10^2$ | $10^2$ |

| MAb No. | EDTA-Cd | EDTA-Zn | EDTA-Cu | EDTA-Pb |
|---|---|---|---|---|
| 2050/174 | $10^3$ | $10^3$ | $10^3$ | $5 \times 10^3$ |
| 2050/531 | $10^3$ | $10^3$ | $10^2$ | $10^5$ |
| 2050/532 | $10^3$ | $10^3$ | $5 \times 10^3$ | $10^5$ |
| 2050/534 | $10^2$ | $10^3$ | $10^3$ | $5 \times 10^3$ |
| 2050/535 | $10^2$ | $10^2$ | $10^2$ | $10^2$ |

TABLE 1

Peptide linkers with relevant nucleotide sequences

```
              E   P   K   S   C   G   G   E   A   A   P   A
+5' CTCTCTGCAGAGCCCAAATCTTGTGGCGGCGAGGCAGCTCCCGCAG
-3' GAGAGACGTCTCGGGTTTAGAACACCGCCGCTCCGTCGAGGGCGTC

A  A  P  A  A  A  A  A  G  G  Q  V  Q  L  Q  E  S
    CTGCACCCGCAGCAGCCGCAGCAGGCGGGCAGGTCCAACTGCAGGAGAGC 3'
    GACGTGGGCGTCGTCGGCGTCGTCCGCCCGTCCAGGTTGACGTCCTCTCG 5'
```

+ = coding strand
− = complementary strand 10 millimolar solutions of the following metal ions were prepared in double-distilled water:

| | | |
|---|---|---|
| Manganese chloride from Merck | MW 161.88 No. 5934 | Mn ion radious: 80 pm |
| Cadmium sulfate Riedel de Haer | MW 256.5 No. 31145 | Cd ion radious: 97 pm |
| Zinc chloride from Merck | MW 136.28 No. 8816 | Zn ion radius: 74 pm |
| Copper sulfate from Riedel de Haen | MW 159.61 No. 31294 | Cu ion radius: 96 pm |
| Yttrium chloride from Aldrich | MW 303.36 No. 20,491-9 | Y ion radius: 92 pm |
| Lead(II) nitrate from Riedel de Haen | MW 331.20 No. 31137 | Pb ion radius: 120 pm |

Annex 1e

Quantitative assay of inhibition of MAb by DTPA and EDTA

TABLE 6

Mutagenic oligonucleotides:

1) 5'CTTACCTGGG.CATGCCCCGA.GCTCCCGTGG.GCATGT3'
2) 5'AGTGGGGTTT.TCAGCTCTGCAGAG3'

TABLE 7

Mutated hinge exon:

E\/L\/K\/T\/P\/L\ /G\/D\/T\/T\/H\/T\/C
AGAGCTCAAA.ACCCCACTTG.GTGACACAAC.TCACACATGC
       ↓
       G

TABLE 7-continued

Mutated hinge exon:

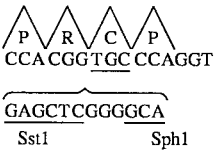

TABLE 8

Jun I oligonucleotide

5'CTACGCTCGG.CTAGAGGAAA.AAGTGAAAAC.
CTTGAAAGCG.CAAAACTCCG.AGCTGGCATC.
CACGGCCAAC.ATGCTCAGGG.AACAGGTGGC.
ACAGCTTAAG.CAGAAAGTCA.TGAACCACCG.
ACCTGCATB3'.

Jun II oligonucleotide

5'CAGGTCGGTG.GTTCATGACT.TTCTGCTTAA.
GCTGTGCCAC.CTGTTCCCTG.AGCATGTTGG.
CCGTGGATGC.CAGCTCGGAG.TTTTGCGCTT.
TCAAGGTTTT.CACTTTTTCC.TCTAGCCGAG.
CGATGAGCT3'.

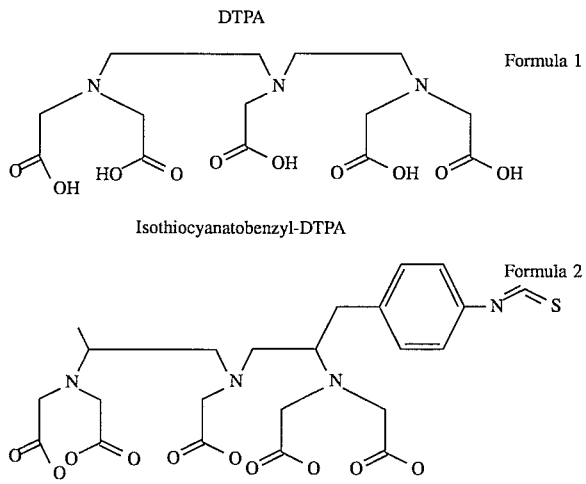

We claim:

1. A bispecific or oligospecific mono- or oligovalent receptor produced by gene manipulation comprising:
    a) a VH and a CH1 region of a first antibody having an antigen binding specificity;
    b) a VH and a CH1 region of a second antibody having an antigen binding specificity, wherein the antigen binding specificity of said first antibody is different from the antigen binding specificity of said second antibody; and
    c) a polypeptide spacer that links the CH1 region of said first antibody to the VH region of said second antibody without impeding association with light chains of said antibodies or antigen binding.

2. A receptor as claimed in claim 1, wherein said receptor further comprises light chains of said first and said second antibodies.

3. A diagnostic composition comprising a receptor as claimed in claim 2.

4. A receptor as claimed in claim 2, wherein said first antibody binds to animal or human tumor-associated antigens.

5. A receptor as claimed in claim 2, wherein said receptor has catalytic or enzymatic activity.

6. A receptor as claimed in claim 2, wherein said first antibody binds to animal or human tumor-associated antigens and said second antibody binds to a chelate.

7. A receptor as claimed in claim 2, wherein a variable region of said first antibody comprises an amino acid sequence of $V_H$ or $V_K$ selected from the group consisting of an amino acid sequence of $V_H$ or $V_K$ of FIG. 22, FIG. 23, FIG. 24, and FIG. 25.

8. A receptor as claimed in claim 4, wherein a variable region of said first antibody comprises an amino acid sequence of $V_H$ or $V_K$ selected from the group consisting of an amino acid sequence of $V_H$ or $V_K$ of FIG. 22, FIG. 23, FIG. 24, and FIG. 25.

9. A receptor as claimed in claim 5, wherein a variable region of said first antibody comprises an amino acid sequence of $V_H$ or $V_K$ selected from the group consisting of an amino acid sequence of $V_H$ or $V_K$ of FIG. 22, FIG. 23, FIG. 24, and FIG. 25.

10. A receptor as claimed in claim 6, wherein a variable region of said first antibody comprises an amino acid sequence of $V_H$ or $V_K$ selected from the group consisting of an amino acid sequence of $V_H$ or $V_K$ of FIG. 22, FIG. 23, FIG. 24, and FIG. 25.

* * * * *